United States Patent [19]

Tanaka et al.

[11] Patent Number: 5,774,575
[45] Date of Patent: Jun. 30, 1998

[54] INSPECTION APPARATUS, AND EXPOSURE APPARATUS AND DEVICE MANUFACTURING METHOD USING THE INSPECTION APPARATUS

[75] Inventors: Hiroshi Tanaka; Michio Kohno, both of Utsunomiya, Japan

[73] Assignee: Canon Kabushiki Kaisha, Tokyo, Japan

[21] Appl. No.: 584,538

[22] Filed: Jan. 11, 1996

[30] Foreign Application Priority Data

Jan. 12, 1995 [JP] Japan .................................. 7-003298
Oct. 26, 1995 [JP] Japan .................................. 7-279018

[51] Int. Cl.$^6$ .................................................. G06R 9/00
[52] U.S. Cl. ........................................ 382/149; 348/130
[58] Field of Search ................................... 382/144, 145, 382/149, 141, 254, 266; 250/572; 348/87, 92, 125, 129, 130; 356/400, 394; 355/53

[56] References Cited

U.S. PATENT DOCUMENTS

| | | | |
|---|---|---|---|
| 4,653,903 | 3/1987 | Torigoe et al. | 355/53 |
| 4,705,940 | 11/1987 | Kohno | 250/201 |
| 4,731,855 | 3/1988 | Suda et al. | 382/149 |
| 4,795,911 | 1/1989 | Kohno et al. | 250/672 |
| 4,831,274 | 5/1989 | Kohno et al. | 250/572 |
| 4,871,257 | 10/1989 | Suzuki et al. | 356/400 |
| 4,886,975 | 12/1989 | Murakami et al. | 250/572 |
| 4,955,062 | 9/1990 | Terui | 382/144 |
| 4,965,842 | 10/1990 | Crossley | 382/144 |
| 4,999,511 | 3/1991 | Kohno | 250/572 |
| 5,017,798 | 5/1991 | Murakami et al. | 250/572 |
| 5,046,109 | 9/1991 | Fujimori et al. | 382/144 |
| 5,105,092 | 4/1992 | Natsubori et al. | 250/572 |
| 5,249,016 | 9/1993 | Tanaka | 355/53 |
| 5,404,410 | 4/1995 | Tojo et al. | 382/144 |
| 5,572,598 | 11/1996 | Wihl et al. | 382/144 |

*Primary Examiner*—Joseph Mancuso
*Attorney, Agent, or Firm*—Fitzpatrick, Cella, Harper & Scinto

[57] ABSTRACT

An inspection apparatus and method includes an illuminator for projecting a light beam onto a substrate having a predetermined pattern formed thereon and a sensor for sensing light from the substrate and photoelectrically converting the light to an electrical signal. The electrical signal has a pattern signal component representing light from the predetermined pattern and a foreign matter signal component representing light from foreign matter on the substrate in the event foreign matter is on the substrate and is sensed by the sensor. The apparatus also includes a converter for converting the electrical signal output by the sensor into a digital signal having a pattern signal component and a foreign matter signal omponent in the event the electrical signal output by the sensor has a foreign matter signal component. The apparatus also includes a processor for performing calculation processing on the digital signal for discriminating the digital foreign matter signal component from the digital pattern signal component in the event the digital signal has a foreign matter signal component.

38 Claims, 18 Drawing Sheets

C1 (C)

C2 (S)

N

C3 (S/N)

C4 (C/N)

C5 (CS/N)

C6

INSPECTION APPARATUS, AND EXPOSURE APPARATUS AND DEVICE MANUFACTURING METHOD USING THE INSPECTION APPARATUS

BACKGROUND OF THE INVENTION

1. Field of the Invention

This invention relates to an inspection apparatus, and more particularly, to an inspection apparatus which is suitable when detecting foreign matter (opaque dust or the like), other than a transfer pattern, which adheres to a substrate, such as a reticle, a photomask or the like, in a semiconductor manufacturing process using an exposure transfer technique, and to application fields using such an apparatus.

2. Description of the Related Art

In a process for manufacturing devices, such as IC's (integrated circuits), LSI's (large-scale integrated circuits) or the like, the devices are manufactured by transferring a circuit pattern for exposure formed on a substrate, such as a reticle, a photomask or the like, onto the surface of a wafer, on which a resist is coated, using a semiconductor printing apparatus (a stepper or a mask aligner).

At that time, if foreign matter, such as dust or the like, is present on the surface of the substrate, the foreign matter is simultaneously transferred during the transfer, thereby causing a decrease in the production yield in device manufacture. Particularly when repeatedly printing a circuit pattern on the surface of a wafer using a reticle according to a step-and-repeat method, a single piece of foreign matter present on the surface of the reticle is printed on a plurality of positions on the surface of the wafer, thereby causing a great decrease in the production yield in device manufacture.

Accordingly, it is indispensable to detect presence of foreign matter on the surface of a substrate in a device manufacturing process, and various inspection methods have been proposed. For example, in a method shown in FIG. 14, a laser beam is projected onto a substrate 5, such as a reticle or the like, obliquely from above with an incident angle $\alpha 0$ (see FIG. 15(B)) to scan the substrate 5 in a direction B1–B2 forming an angle $\beta$ ( with respect to a lateral direction C1–C2. As shown in FIG. 15(B), only scattered light having an angle of reflection $\alpha 1$ with respect to the substrate 5 from among scattered light from foreign matter returned to the incident side within the incident plane is sensed. In FIG. 14, a laser beam from a laser 1 is projected onto the substrate 5 via a scanning mirror 2 and a lens 4. Scattered light from the foreign matter reaches a photosensing unit 9 via a lens 6, a mirror 7 and a lens 8. FIG. 15(A) illustrates the principle of this method. A circuit pattern on the substrate 5 is mostly formed by lines in the vertical direction (Vl–V2) and in the horizontal direction (L1–L2). When the laser beam is projected onto this pattern, diffracted light from the pattern travels in a direction orthogonal to the lines, i.e., in the direction L1–L2, or the direction V1–V2. In this method, the scanning direction of the laser beam with respect to the substrate 5 makes, for example, an angle $\beta$ with respect to the vertical direction V1–V2 of the substrate 5. Since diffracted light from the circuit pattern is mainly in the vertical and horizontal directions of the substrate 5, only a very small percentage of the diffracted light from the circuit pattern is sensed, while a relatively large percentage of diffracted light from the foreign matter having an isotropic light scattering property is sensed. Accordingly, the presence of foreign matter is detected by comparing the magnitudes of signals from the photosensing unit 9 with each other.

FIG. 16 illustrates an optical system of a conventional inspection apparatus which utilizes the isotropic light scattering property of foreign matter. In FIG. 16, a light beam from a laser 10 is alternately projected onto one of both surfaces of a substrate 15 via a scanning mirror 11 and a lens 12 by guiding the light beam upward or downward by inserting or retracting a mirror 13, respectively, and scans the substrate 15 due to the rotation or vibration of the scanning mirror 11. A plurality of photosensing units 16, 17 and 18 are provided at positions separated from the optical paths of directly reflected light and transmitted light from the substrate 15, and the presence of foreign matter on the substrate 15 is detected using output signals from these photosensing units 16, 17 and 18. Since diffracted light from a circuit pattern has a strong directional property, outputs from the respective photosensing units have different values. However, when the light beam is projected onto foreign matter, since the incident light beam is isotropically scattered by the foreign matter, outputs from the respective photosensing units have substantially the same value. Accordingly, the presence of foreign matter is detected by comparing the output values of the respective photosensing units with one another.

FIG. 17 illustrates an optical system of another conventional inspection apparatus which utilizes the property that foreign matter disturbs the polarizing characteristics of an incident light beam. In FIG. 17, a light beam from a laser 10 is converted into a light beam having a predetermined state of polarization via a polarizer 19, a scanning mirror 11 and a lens 12, is then guided upward or downward by inserting or retracting a mirror 13, respectively, and scans a substrate 15 due to the rotation of the scanning mirror 11 while alternately projecting the light beam onto one of both surfaces of the substrate by one of two mirrors 14 and 45. Two photosensing units 21 and 23 having polarizers 20 and 22 disposed in front thereof, respectively, are provided at positions separated from the optical paths of directly reflected light and transmitted light from the substrate 15. The difference between the amounts of received light due to the difference between the ratios of polarization of diffracted light from the circuit pattern on the substrate 15 and direct light from foreign matter is detected by the two photosensing units 21 and 23, and the foreign matter is thereby discriminated from the circuit pattern on the substrate 15.

In current semiconductor device manufacturing methods, an exposure apparatus using an i-line as exposure light requires an exposure technique for a line width of 0.35$\mu$m. In an exposure apparatus using deep-UV light, such as laser light from an examiner laser having a shorter wavelength, or the like, the line width becomes narrower, for example, 0.2$\mu$m. In the case of an exposure apparatus using a reduction projection lens, a circuit pattern on a reticle is generally subjected to reduction projection to a size equal to $\frac{1}{5}$ of the size of the reticle. Hence, in the case of a reticle having a target line width of 0.35 $\mu$m, the minimum particle size of foreign matter to be detected is about 0.7–0.8 $\mu$m. In the case of a reticle having a target line width of 0.2$\mu$m, the minimum particle size becomes about less than 0.5 $\mu$m. Accordingly, in foreign-matter inspection for a reticle having a target exposure line width of 0.2$\mu$m, it is necessary to discriminate a signal output from foreign matter from a noise signal output from a circuit pattern with the above-described accuracy.

However, the above-described conventional inspection apparatuses cannot satisfy such a requirement because of the following reasons. That is, as the particle size of foreign matter to be inspected becomes smaller, the intensity of scattered light or direct light from the foreign matter becomes smaller, and the level of a signal output after photoelectric conversion by the photosensing units becomes smaller. In general, signal-output-level characteristics as a function of particle sizes as shown in FIGS. 18(A) and 18(B) are known. FIG. 18(A) illustrates the relationship between the particle size of foreign matter and the signal level. In FIG. 18(A), the abscissa represents the particle size, and the ordinate represents the signal level (voltage). FIG. 18(B) illustrates signal levels (voltages) (the ordinates) for various circuit patterns A, B, C, D, E, F, G and H (the abscissa). As can be understood from FIGS. 18(A) and 18(B), since the levels of signal outputs from circuit patterns substantially equal the level of a signal output from foreign matter having a particle size of about 0.5 $\mu$m, it is difficult to discriminate foreign matter having a particle size equal to or less than 0.5 $\mu$m from a circuit pattern in the above-described conventional methods.

SUMMARY OF THE INVENTION

The present invention has been made in consideration of the above-described problems.

It is an object of the present invention to provide a high-precision inspection apparatus capable of assuredly detecting foreign matter having such a small particle size that a signal from it is masked by circuit-pattern noise in conventional methods, and inspecting foreign matter which will influence the production yield during actual exposure.

It is another object of the present invention to provide applications using such an inspection apparatus, such as an exposure apparatus, a method for manufacturing devices having fine patterns, and the like.

According to one aspect, the present invention which achieves these objectives relates to an inspection apparatus, comprising illuminating means, light sensing means, converting means, and processing means. The illuminating means projects a light beam onto a substrate having a predetermined pattern formed thereon. The light sensing means senses light from the substrate and photoelectrically converts the light to an electrical signal. The electrical signal has a pattern signal component representing light from the predetermined pattern and a foreign matter signal component representing light from foreign matter on the substrate in the event foreign matter is on the substrate and is sensed by the light sensing means. The converting means converts the electrical signal output by the light sensing means into a digital signal having a pattern signal component and a foreign matter signal component in the event the electrical signal output by the light sensing means has a foreign matter signal component. The processing means performs calculation processing on the digital signals for discriminating the digital foreign matter signal component from the digital pattern signal component.

According to another aspect, the present invention which achieves these objectives relates to an exposure apparatus comprising an inspection apparatus and means for performing exposure and transfer processing using the inspection substrate inspected by the inspection apparatus. The inspection apparatus comprises illuminating means, light sensing mans, converting means and processing means. The illuminating means projects a light beam onto a substrate having a predetermined pattern formed thereon. The light sensing means senses light from the substrate and photoelectrically converts the light to an electrical signal. The electrical signal has a pattern signal component representing light from the predetermined pattern and a foreign matter signal component representing light from foreign matter on the substrate in the event foreign matter is on the substrate and is sensed by the light sensing means. The converting means converts the electrical signal output by the light sensing means into a digital signal having a pattern signal component and a foreign matter signal component in the event the electrical signal output by the light sensing means has a foreign matter signal component. The processing means performs calculation processing on the digital signals for discriminating the digital foreign matter signal component from the digital pattern signal component.

According to another aspect, the present invention relates to a method comprising the steps of projecting a light beam onto a substrate having a predetermined pattern formed thereon, and sensing light from the substrate and photoelectrically converting the light to an electrical signal having a pattern signal component representing light from the predetermined pattern and a foreign matter signal component representing light from foreign matter on the substrate in the event foreign matter is on the substrate and is sensed by the sensing step. The method further comprises the step of converting the electrical signal produced in the sensing step into a digital signal having a pattern signal component and a foreign matter signal component in the event the electrical signal output in the sensing step has a foreign matter signal component. The method also comprises the step of performing calculation processing on the digital signal for discriminating the digital foreign matter signal component from the digital pattern signal component in the event the digital signal has a foreign matter digital component.

The foregoing and other objects, advantages and features of the present invention will become more apparent from the following detailed description of the preferred embodiments taken in conjunction with the accompanying drawings.

DETAILED DESCRIPTION OF THE PREFERRED EMBODIMENTS

First Embodiment

Figure 1:
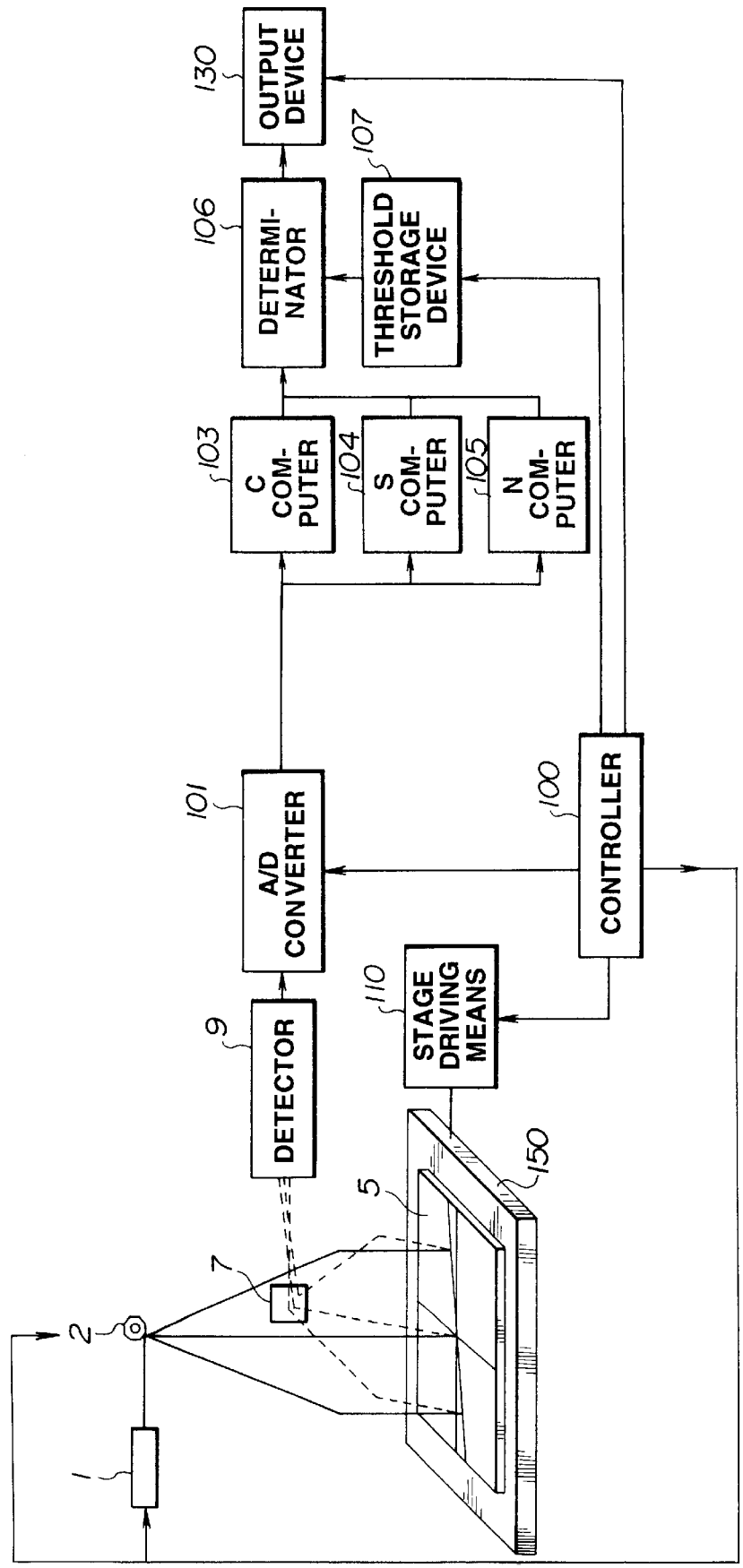
FIG. 1 is a schematic block diagram illustrating the configuration of an apparatus for inspecting foreign matter on a reticle according to a first embodiment of the present invention.

A description will now be provided of the configuration of an inspection apparatus according to a first embodiment of the present invention with reference to FIG. 1. In FIG. 1, a light beam emitted from a laser light source 1 scans a reticle substrate 5 by means of a rotating polygonal mirror 2. Scattered light from foreign matter on the substrate 5 is reflected by a mirror 7 to a detector 9 where it is converted into an electrical signal by a photoelectric transducer provided within the detector 9. The electrical analog signal obtained as a result of photoelectric conversion is converted into a digital signal by an A/D (analogto-digital) converter 101. The digital signal comprises 6–10 bits. The laser beam for scanning is condensed so that the cross section of the beam has a Gaussian intensity distribution.

Figure 2A:
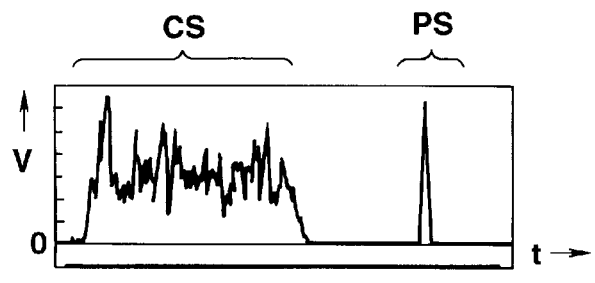
FIGS. 2(A) through 2(H) are graphs illustrating results of signal processing in the first embodiment.

The A/D converter 101 is synchronized with the polygonal mirror 2, and performs sampling at a predetermined time interval under the control of a controller 100 which also controls laser light source 1 and rotating mirror 2. In FIG. 1, when the reticle substrate 5 is subjected to single scanning from right to left, the digital signal after A/D conversion has a signal wave form as shown in FIG. 2(A). In FIG. 2(A), the abscissa represents time, and the ordinate represents a signal level (a voltage). Since the light beam performs scanning at a constant speed, the abscissa also represents the position of the light beam on the substrate 5.

The detection signal has the following general characteristics.

1) A signal from foreign matter provides an electrical waveform which has a Gaussian distribution on the time base.

2) A signal from a circuit pattern is a random noise signal.

3) The intensity of the signal from foreign matter is weaker as the particle size of the foreign matter is smaller. However, the width of the signal does not change.

4) When foreign matter adheres to a circuit pattern, the intensity of the obtained signal substantially corresponds responds to noise 30 foreign matter, so that the signal level increases.

The reason for the above-described characteristic 1) is as follows. That is, the scanning beam is condensed so that the intensity of the beam has a Gaussian distribution. Hence, when a laser beam having a diameter of about 20$\mu$m is projected onto foreign matter which is sufficiently smaller than the diameter of the light beam (equal to or less than 1 $\mu$m), the intensity of light illuminating the foreign matter also has a Gaussian distribution. As a result, the intensity of scattered light generated by the foreign matter also has a Gaussian distribution.

Conventionally, when the particle size of foreign matter is small, the signal level of scattered light from the foreign matter is reduced, and therefore it is impossible to discriminate a foreign-matter signal from a noise signal from a circuit pattern. FIG. 2(A) illustrates such a state. In FIG. 2(A), CS represents a noise signal from a circuit pattern, and pS represents a signal from foreign matter. In the present embodiment, three types of signal processing are performed utilizing the above-described characteristics, and discrimination between a circuit-pattern signal and a foreign-matter signal is performed by combining results of the three types of signal processing.

The above-described three types of signal processing will now be described in detail. First, a description will be provided of signal processing, serving as basic processing.

processing 1 Template matching processing (correlation calculation)

Utilizing the characteristic that a signal from foreign matter has a Gaussian distribution, template matching processing (correlation calculation) between templates of the Gaussian distribution and a signal waveform is performed. A foreign-matter signal is emphasized according to this processing. The calculation formula is as follows:

$$C(x) = \sum_{i=-n}^{n} D(x+i)T(i). \tag{1}$$

This expression indicates the correlation between templates of 2n+1 points and signal data, where T(i) represents templates, and D(x) represents stored signal data received from A/D converter 101 and stored in computer 103, and C(x) represents the result of the correlation.

In practice, in order to shorten the processing time period, the interval between templates is lengthened, and the following calculation is performed:

$$C(x) = \sum_{i=-n'}^{n'} D(x+i*p)T(i). \tag{2}$$

Figure 2B:
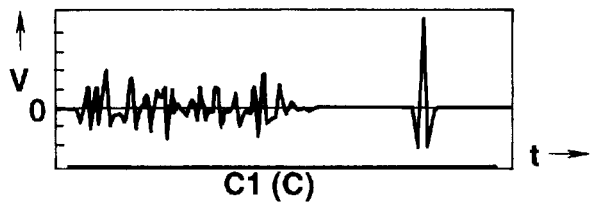

Since the interval between templates is multiplied by p, the number of templates is reduced to 1/p compared with the case of expression (1). FIG. 2(B) illustrates a result of template matching. Template coefficients at that time are T(-3)=-23, T(-2)=-16, T(-1)=19, T(0)=40, T(1)=19, T(2)=-16, and T(3)=-23.

processing 2 Signal extraction processing

Figure 2C:
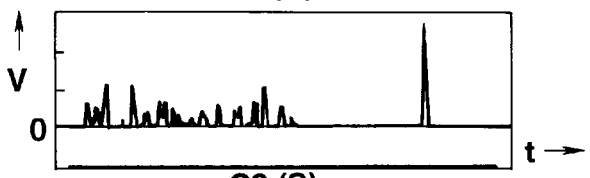

In order to perform signal extraction, utilizing the characteristic that a signal of scattered light from foreign matter has a Gaussian distribution, the difference between the top and the bottom of a signal is obtained. Also, by utilizing the fact that the width of the signal from foreign matter is substantially the same irrespective of the particle size, the interval between the top and the bottom of a signal adjusted to a foreign-matter signal is set. The calculation formula for the signal is as follows:

$$S(x) = (D(x)-D(x-b))+(D(x)-D(x+b)) \quad (3)$$

if $S(x) < 0$, $S(x) = 0$, where $S(x)$ represents a signal, and b represents a preset interval between the top position and the bottom position. Since a circuit pattern produces a noise signal, the difference between the levels of the top and the bottom of the signal is smaller than in the case of a foreign-particle signal. That is, even if the noise level and the level of a signal from foreign matter is the same before signal extraction processing, the signal from the foreign matter is emphasized by extracting the signal component according to the above-described expression. The sign of $S(x)$ is always positive at the position of the signal representing scattered light from the foreign matter. FIG. 2(C) illustrates an example of extraction of signal components.

processing 3 Noise extraction processing

Figure 2D:
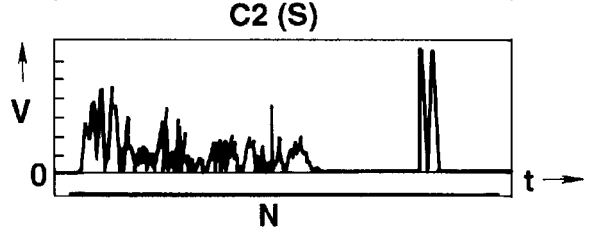
Figure 2E:
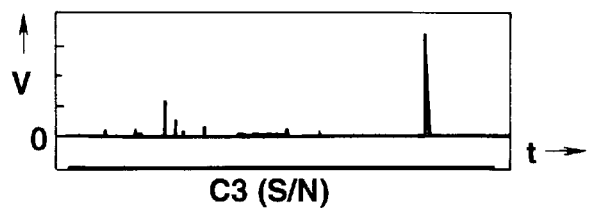
Figure 2F:
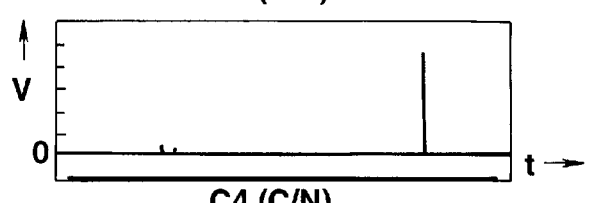
Figure 2G:
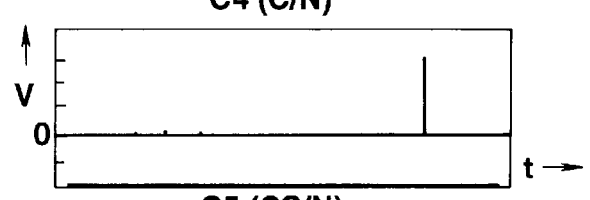
Figure 2H:
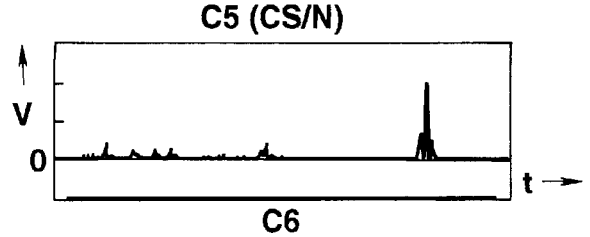

In order to extract noise, utilizing the characteristic that a Gaussian distribution is symmetrical, the difference between signal levels at symmetrical positions is calculated. The calculation formula for noise extraction is as follows:

$$N(x) = \sum_{i=1}^{n} |D(x+si) - D(x-si)|, \quad (4)$$

where $N(x)$ represents noise. n symmetrical positions are preset, and each position is present at a distance si from the center. The value of n may be 1. In such a case, the bottom position used for the signal may be used. Expression (4) has a large value at a position where the signal is asymmetrical or at a position where the noise component is large. On the other hand, expression (4) has a small value at a position of a foreign-matter signal having a Gaussian distribution. FIG. 2(D) illustrates an example of extraction of a noise component.

Next, a description will be provided of a method of discriminating foreign matter from a circuit pattern by combining the results of the above-described three basic types of signal processing. The following five results can be derived from results of the three types of signal processing:

$$C1(x) = C(x) \quad (5)$$

$$C2(x) = S(x) \quad (6)$$

$$C3(x) = S(x)/N(x) \quad (7)$$

$$C4(x) = C(x)/N(x) \quad (8)$$

$$C5(x) = C(x)S(x)/N(x) \quad (9)$$

$$C6(x) = C(x)C(x) \quad (10)$$

Any of the above-described five methods can discriminate a foreign-matter signal from a circuit-pattern signal. FIGS. 2(E), 2(F), 2(G) and 2(H) illustrate the results of C3, C4, C5 and C6, respectively.

It can be understood that excellent discrimination can be performed particularly by C5. C5 represents a result of synthesizing all of the above-described three types of basic processing, and is the most effective method for discriminating a foreign-matter signal. As is apparent from FIG. 2(G), a signal which could not be discriminated by the conventional methods is discriminated with a level difference of at least 20 times. In other words, the level of the foreign matter signal is twenty times the level of the noise signal from a circuit pattern. The same signal can be discriminated with level differences of at least 2.5 times and 10 times by C3 and C4, respectively.

When it is intended to shorten the processing time, Cl or C2 may be selected. When it is intended to increase accuracy in discrimination, one of C3, C4, C5 and C6 may be selected.

Next, a calculation processing system for performing the above-described signal processing will be described in detail. Signals which are time serially obtained are subjected to template matching processing time serially by a C computer 103, to obtain $C(x)$. The signal $S(x)$ is calculated by an S computer 104. The noise $N(x)$ is calculated by an N computer 105. All three computers receive the output of A/D converter 101. Then, a determinator 106 which receives the output from computers 103–105, calculates one of $Cl(x)$ through $C6(x)$. Thus, a foreign-matter signal is emphasized, and other signals, particularly a noise signal from a circuit pattern, can be more easily discriminated. Selection from among $Cl(x)$ through $C6(x)$ by determinator 106 is predetermined by a controller 100, and optimum processing is appropriately set. In order to discriminate a foreign-matter signal from other signals, a threshold stored in a threshold storage device 107 is consulted by the determinator 106 under the control of a controller 100. That is, a signal greater than the threshold is determined to be from foreign matter, and a signal less than the threshold is determined to be not from foreign matter. Since the magnitude of a signal differs depending on the particle size of the foreign matter, it is possible to discriminate the particle size of foreign matter by setting a plurality of thresholds. After the determinator 106 determines the presence of foreign matter, the result is transmitted to an output device 130. At the same time, the position of the light beam on the substrate is changed by finely moving a stage 150, which mounts the substrate 5, using stage driving means 110 under the control of controller 100. By scanning the substrate 5 with the laser beam a plurality of times while finely moving the reticle substrate 5, detecting foreign matter using a signal obtained by photoelectric conversion at each scanning according to one of the above-described methods, and displaying the position of foreign matter and the scanning position at each scanning on the output device 130, the position of foreign matter on the entire reticle is displayed on the output device 130 under the control of controller 100.

Figure 3:
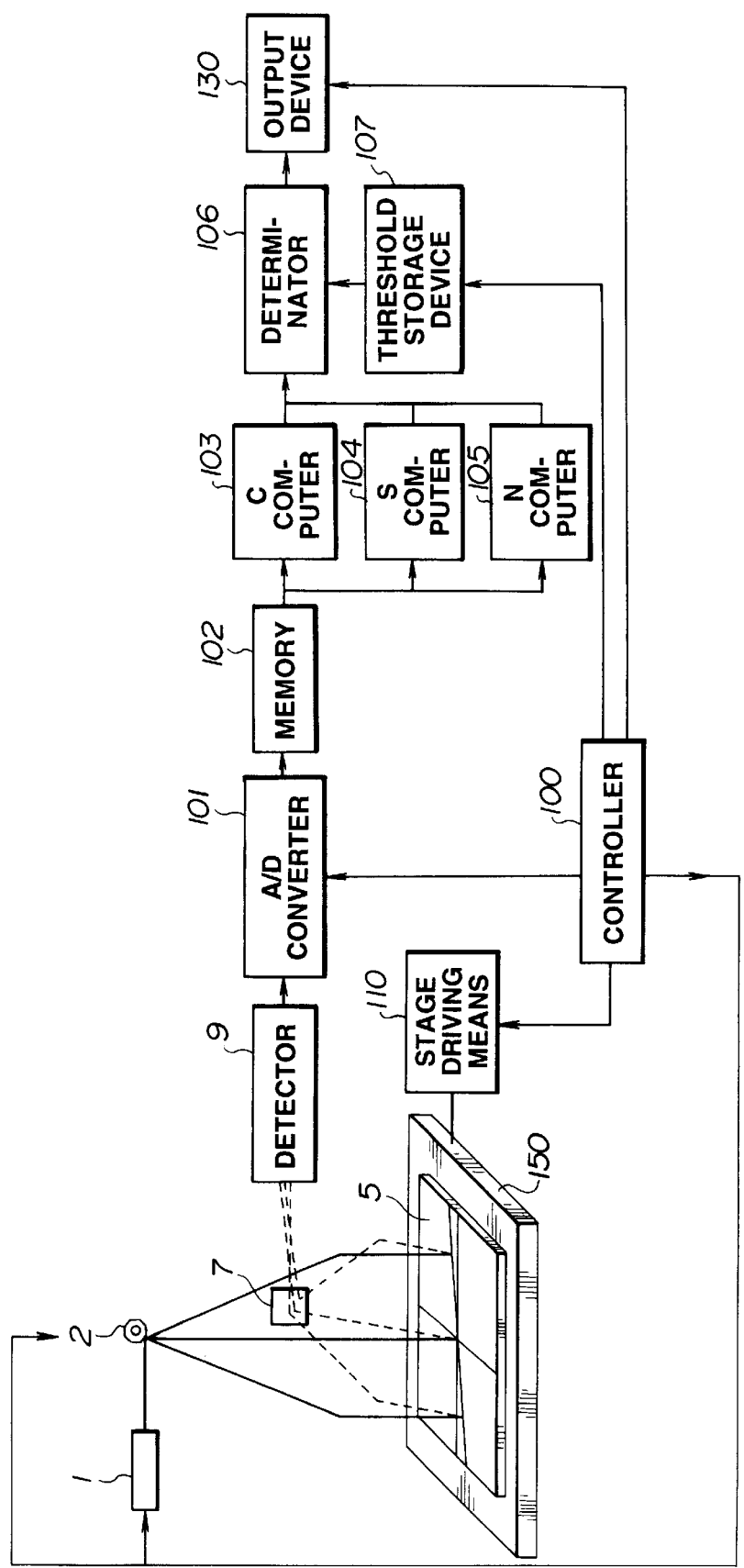
FIG. 3 is a schematic block diagram illustrating the configuration of an apparatus for inspecting foreign matter on a reticle according to a modification of the first embodiment.

In the present embodiment, the C computer 103, the S computer 104 and the N computer 105 time serially process digital signals which are time serially obtained. Accordingly, although more or less delayed from the timing of A/D conversion, the result is obtained substantially in synchronization with the timing of the A/D conversion. If the C computer 103, the S computer 104 and the N computer 105 cannot time serially process signals, for example, if the processing times of these computers cannot follow the speed of the A/D conversion, digital signals obtained by the A/D conversion may be processed after first storing the signals in a memory. The same result can be obtained by such an approach. FIG. 3 illustrates the configuration of a calculation processing system in such a case in which the signals from the A/D converter are stored in a memory 102. In the embodiment shown in FIG. 3 the same reference numerals as those used in FIG. 1 denote the same elements.

When scanning by a polygonal mirror motor of mirror 2 includes a time to scan the reticle substrate 5 and a setting time (flyback time) for the next scanning, a result corresponding to single scanning is obtained by first storing signals in the memory 102 and then processing the signals by the C computer 103, the S computer 104 and the N computer 105 having a processing time which is slower than the speed of A/D conversion. For example, if the scanning time is 1 msec and the flyback time is 3 msec, the entire processing time is 4 msec. Hence, a processing time equal to four times the speed of A/D conversion is allowed.

Although in the present embodiment, one of the results of Cl–C6 is selected by determinator 106, various modifications obtained by combining C(x), S(x) and N(x) can be considered. As for C(x), templates having various coefficients can be considered. For the purpose of emphasizing the characteristics of a foreign-matter signal, there is no limitation in template coefficients, parameters, and combinations of C(x), S(x) and N(x).

Figure 16:
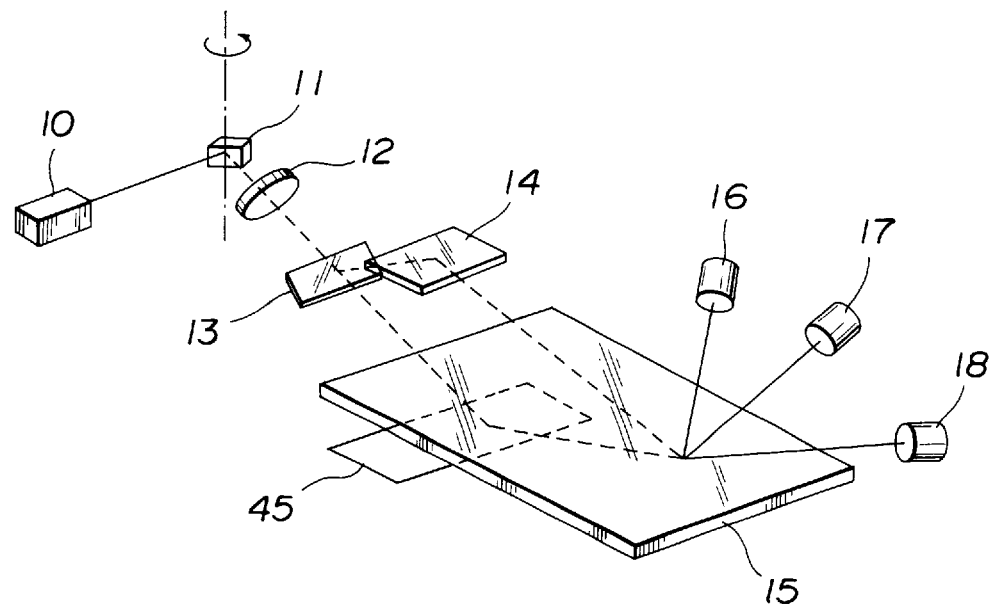
FIG. 16 is a schematic diagram illustrating an optical system of another conventional apparatus for inspecting foreign matter on a reticle.
Figure 17:
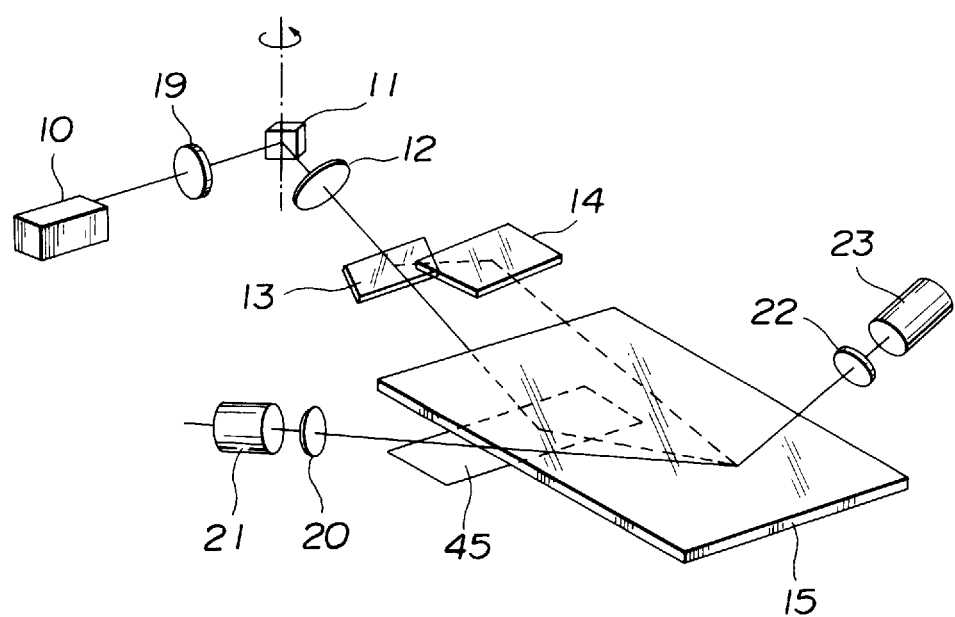
FIG. 17 is a schematic diagram illustrating an optical system of still another conventional apparatus for inspecting foreign matter on a reticle.
Figure 18A:
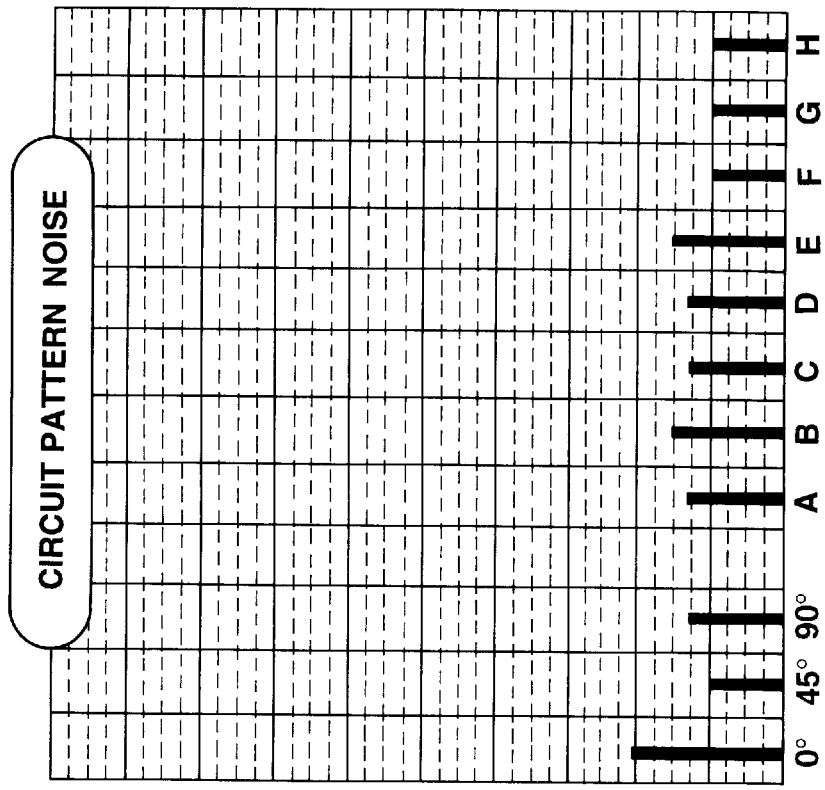
FIGS. 18(A) is a graph illustrating the relationship between the level of the output signal and the particle size of foreign matter.
Figure 18B:
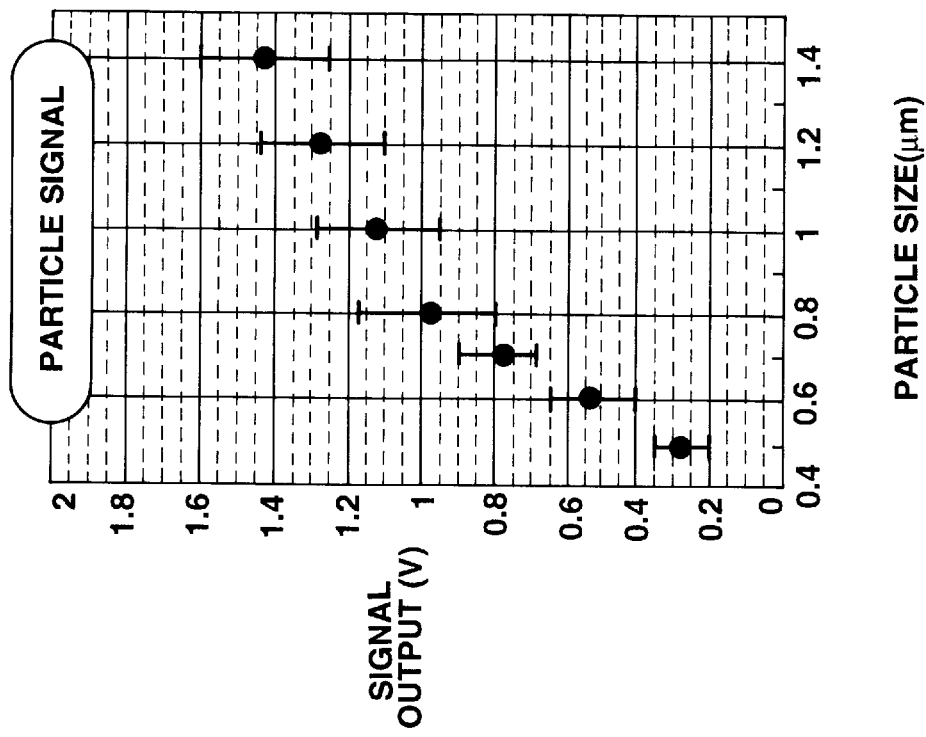
FIG. 18(B) is a graph illustrating the relationship between the level of the output noise signal and the circuit pattern.

The above-described signal processing of the present embodiment may also be applied to detection signals obtained in the optical systems shown in FIGS. 16 and 17, and the same effects as in the present embodiment can also be obtained.

Second Embodiment

Figure 4:
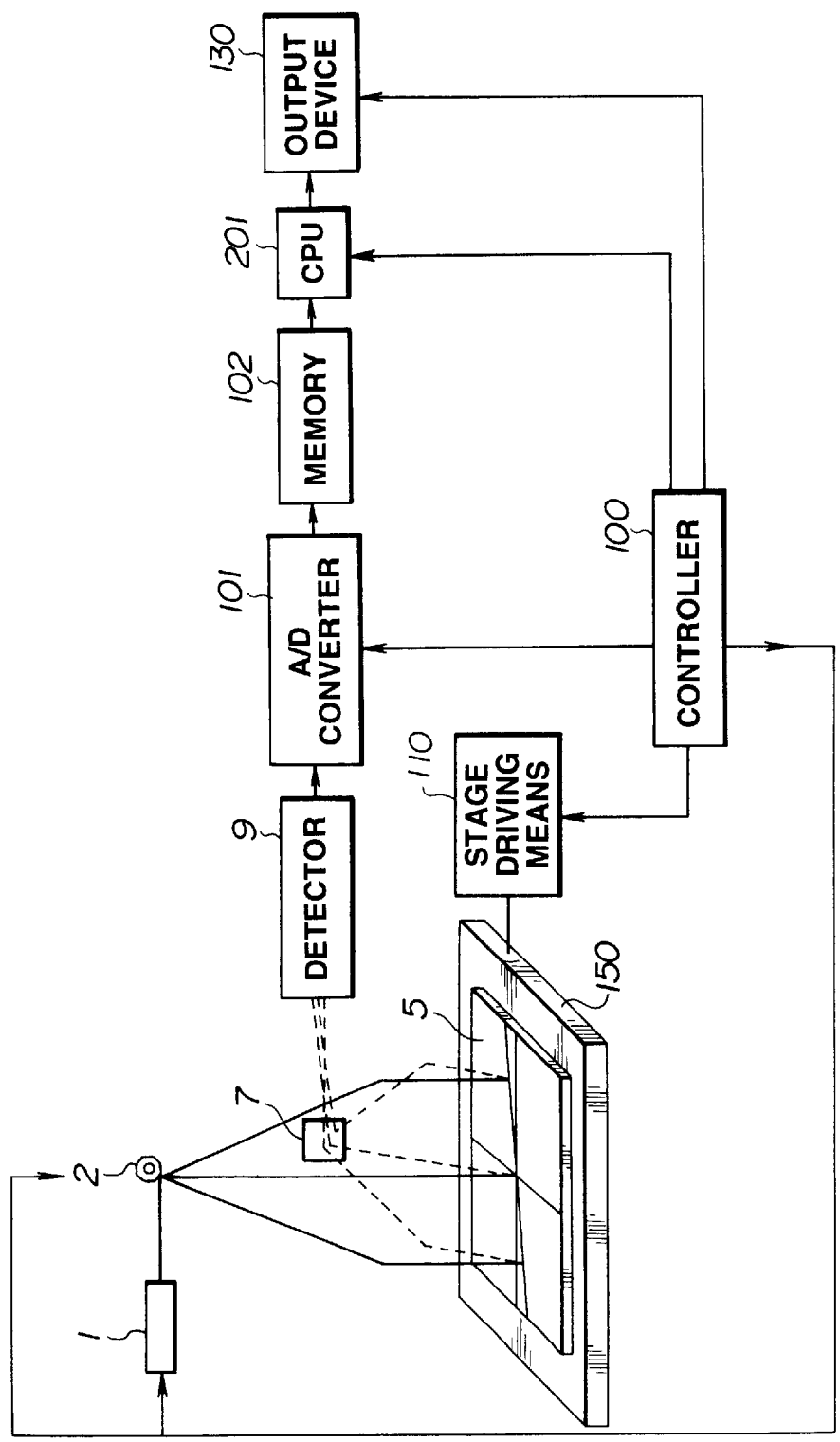
FIG. 4 is a schematic block diagram illustrating the configuration of an apparatus for inspecting foreign matter on a reticle according to a second embodiment of the present invention.

FIG. 4 illustrates the configuration of an inspection apparatus according to a second embodiment of the present invention. In this embodiment the same reference numerals as those used in FIGS. 1 and 2 denote the same elements. In FIG. 4, since the optical system has the same structure as in the first embodiment, a description thereof will be omitted. The second embodiment has the feature that the C computer, the S computer, the N computer, the determinator and the threshold storage device described in the first embodiment are not provided as independent units, but comprise a single CpU (central processing unit) 201 which performs these functions under the control of the controller 100. Since the details of the processing are the same as in the first embodiment, a description thereof will be omitted. The shape of the templates can be easily changed by changing a program because the CPU 201 performs the processing. Although a microprocessor may be used as the CPU 201, a DSP (digital signal processor) designed so as to be suitable for signal processing may also be utilized. By using a DSP, continuous signal processing can be performed at a high speed.

When performing processing by the CPU, if the processing speed of the CPU is high, it is possible to directly receive digital signals obtained by A/D conversion in the CPU 201, and to output the results of processing. Accordingly, it is unnecessary to first store digital signals obtained by A/D conversion in a memory 102. When the processing speed of the CPU is low, processing is performed by first storing digital signals obtained by A/D conversion in a memory 102.

When scanning with a polygonal-mirror motor of mirror 2 includes of a time to scan the reticle substrate 5 and a setting time (flyback time) for the next scanning, a result corresponding to single scanning is obtained. For example, if the scanning time is 1 msec and the flyback time is 3 msec, the entire processing time is 4 msec. Hence, a processing time equal to four times the speed of A/D conversion is allowed.

The signal processing of the present embodiment may also be applied to detection signals obtained in the optical systems shown in FIGS. 16 and 17, and the same effects as in the present embodiment can also be obtained.

Figure 5:
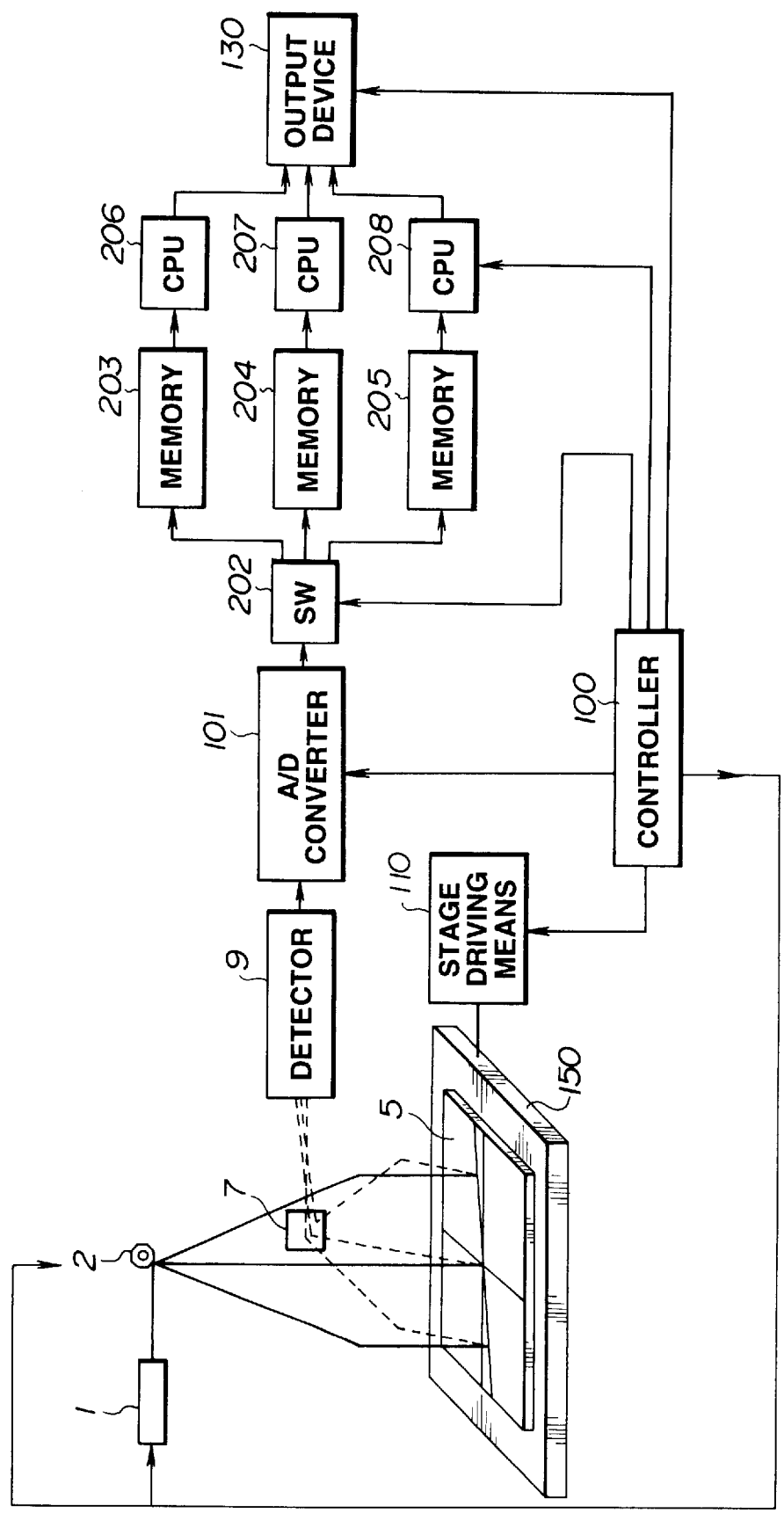
FIG. 5 is a schematic block diagram illustrating the configuration of an apparatus for inspecting foreign matter on a reticle according to a third embodiment of the present invention.

Third Embodiment FIG. 5 illustrates the configuration of an inspection apparatus according to a third embodiment of the present invention.

In this embodiment the same reference numerals as those used in FIG. 1 denote the same elements. In FIG. 5, since the optical system is the same as in the first embodiment, a description thereof will be omitted. When executing inspection of foreign matter on a glass substrate at a high speed, the scanning time using a polygonal mirror is generally shortened. However, if the processing time of signal processing is longer than the scanning time produced by the polygonal mirror, inspection cannot follow scanning. Accordingly, by performing parallel processing using a plurality of C, S and N computers and determinators, or a pluralilty of CPU's, processing can be performed at a higher speed. In the present embodiment, a description will be provided of a case in which a plurality of CPU's 206–208 are provided. However, the basic concept does not change also when performing parallel processing using a plurality of C, S and N computers and determinators described in the first embodiment.

For example, if the time required for processing signals obtained by one scanning operation with a single CPU corresponds to three scanning operations of the polygonal mirror, parallel processing is performed using three CPU's 206–208. The one scanning operation includes the time required to scan the reticle substrate 5 and the flyback time. In this case, a controller 100 switches the memory to which data is to be transferred by switching a switch SW 202 at every scanning operation by a polygonal mirror 2. After switch 202 transfers data to a memory 203, the CPU 206 connected to that memory starts processing the data therefrom. At the same time, data is transferred by switch 202 to the next memory 204 and the CPU 207 starts processing data therefrom. At the same time, data is transferred by switch 202 to a memory 205 and the CPU 208 starts processing data therefrom. By switching the memory to which data is to be transferred and the CPU for performing processing every time scanning has been completed, parallel signal processing is performed, and inspection can be performed at a high speed.

The signal processing of the present embodiment may also be applied to detection signals obtained in the optical systems shown in FIGS. 16 and 17, and the same effects as in the present embodiment can also be obtained.

Figure 6:
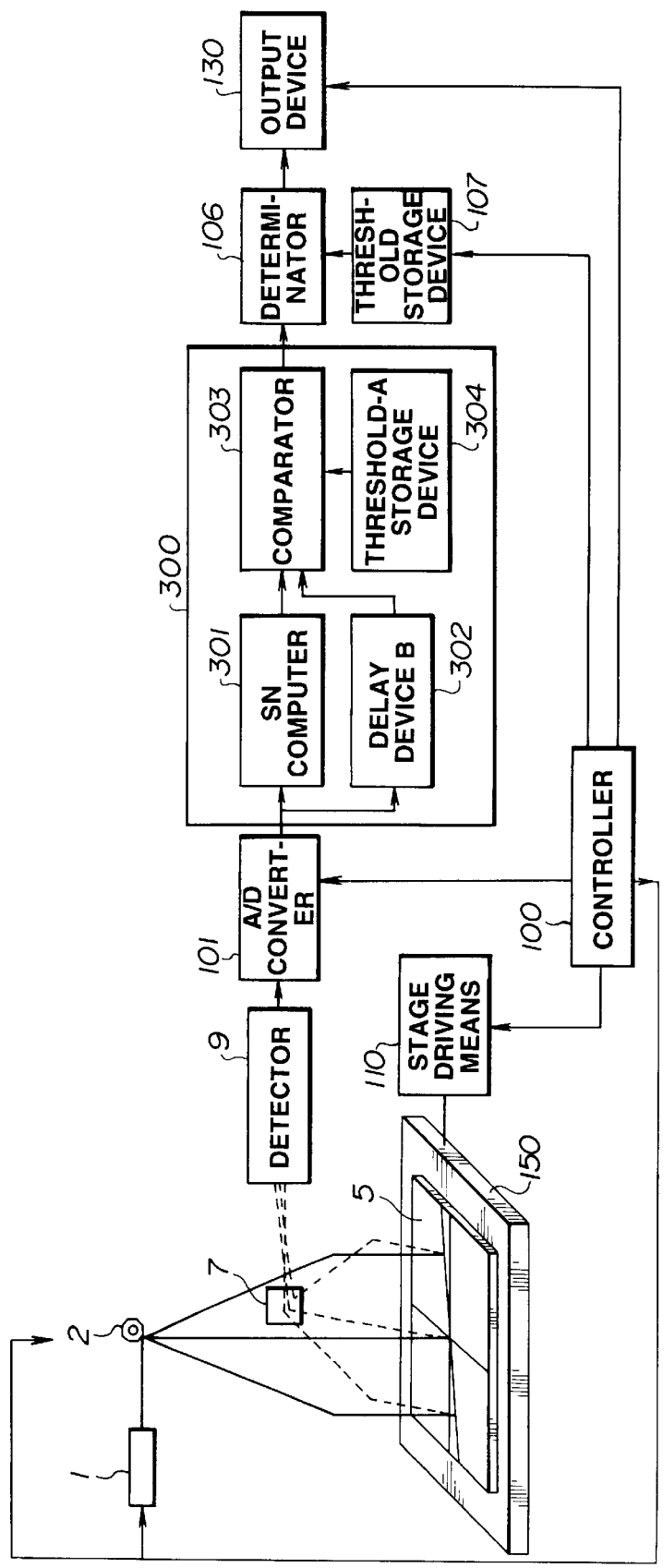
FIG. 6 is a schematic block diagram illustrating the configuration of an apparatus for inspecting foreign matter on a reticle according to a fourth embodiment of the present invention.

Fourth Embodiment FIG. 6 illustrates the configuration of an inspection apparatus according to a fourth embodiment of the present invention. The configuration of the inspection apparatus of the fourth embodiment differs from that of the first embodiment shown in FIG. 1 in that it includes calculation means 300. Since other components are the same as in the first embodiment, the reference numerals used in FIG. 6 that are the same as those used in FIG. 1 denote identical elements and a further description thereof will be omitted. Signal processing in the present embodiment is performed as follows.

Processing 1 Low-frequency-cut filtering

Utilizing the characteristics that a signal from foreign matter has a Gaussian distribution, and the width of the signal is substantially constant, signals having periods longer than the width of the signal from foreign matter are removed from digital signals obtained by A/D conversion. In other words, components having lower frequencies than the frequency of a foreign-matter signal are cut. This lowfrequency-cut processing is performed as follows:

$$LC(t) = \sum_{i=-n}^{n} X(t+i)T(i). \tag{11}$$

This expression indicates the correlation between templates of 2n+1 points and signal data, where T(i) represents filter coefficients, X(t) represents stored signal data generated by detector 9 and converted to digital form by A/D converter 101 and stored in calculation means 300, and LC(t) represents the result of removal of low-frequency components.

In order to shorten the processing time period, the interval between filter coefficients is lengthened, and the following calculation is performed:

$$LC(t) = \sum_{i=-n'}^{n'} X(t + i*p)T(i). \quad (12)$$

Figure 7:
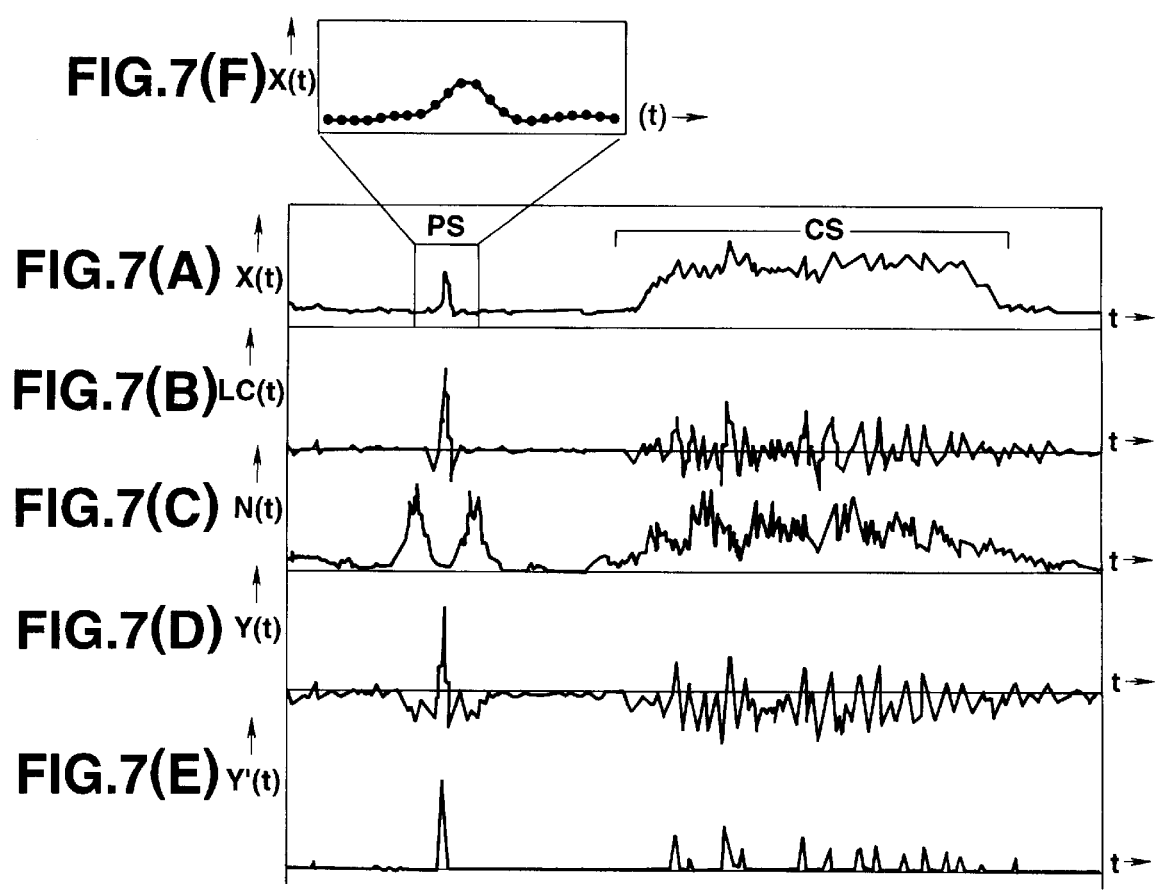
FIGS. 7(A) through 7(E) are graphs illustrating results of signal processing in the fourth embodiment.

Since the interval between filter coefficients is multiplied by p, the number of filter coefficients, i.e., the filter size is reduced to 1/p compared with the case of expression (11). FIG. 7(B) illustrates a result of low-frequency-cut filtering. In FIG. 7(B) the abscissa represents time and the ordinate represents LC. template coefficients at that time used to generate the graph shown in FIG. 7(B) are T(-2)=-1, T(-1)=-1, T(0)=4, T(1)=-1, T(2)=-1, and the interval p=4. Processing 2 Noise component extraction Within signals obtained by removing low-frequency components in the processing 1, impulse noise having frequencies higher than the frequency of the foreign-matter signal remains. Such noise is produced, for example, in the detector 9. Extraction of the noise components of the signals is performed as follows:

$$N(t) = \sum_{i=-n'}^{n'} |LC(t + i*p_2)|Tn(i). \quad (13)$$

FIG. 7(C) illustrates an example of noise extraction. NCT represents the value of noise at time t, Tn(i) represents template coefficients for different values of i, and LC represents the signal detected by the detector 9 after the removal of the low frequency components.

In FIG. 7(C) the abscissa represents time and the ordinate represents N(t). Template coefficients at that time used to generate the graph as shown in FIG. 7(B) are Tn(-10) =1, Tn(-9)=1, Tn(-7)=1, Tn(-6-6)=0, Tn(7)=1, Tn(8)=1, Tn(9) =1, and Tn(10) =1, and the interval at that time is $p_2=2$.

In order to discriminate a signal representing light reflected from foreign matter from a signal representing light reflected from a circuit pattern using the abovedescribed two types of processing, the following processing is performed.

$$Y(t)=LC(t)-N(t) \quad (14)$$

That is, after removing components representing scattered light from a circuit pattern, and the like, noise is removed by integrating noise components in the resultant signal. FIG. 7(D) illustrates an example of the result of this processing. In FIG. 7(D) the abscissa represents time the the ordinate represents Y(t). Of course, among Y(t), components whose levels are equal to or less than 0 are meaningless as a detection signal. FIG. 7(E) illustrates the final processing signal Y'(t), where the abscissa represents time and the ordinate represents Y'(t).

$$Y'(t) = \begin{cases} Y(t) & \text{when } Y(t) > 0 \\ 0 & \text{when } Y(t) \leq 0. \end{cases} \quad (15)$$

In FIG. 7(A), the S/N ratio of a signal pS representing light reflected from foreign matter to a signal CS representing light reflected from a circuit pattern is equal to or less than 1. In FIG. 7(A) the abscissa represents time and the ordinate represents X(t). FIG. 7(F) is an enlarged view of a part of signal pS showing the points making up signal pS. On the other hand, in FIG. 7(E), the S/N ratio increases to a value equal to or greater than 2. That is, signals which could not have been discriminated by conventional methods can be clearly discriminated in the present embodiment.

A unit for performing the above-described signal processing will now be described in detail with reference to FIG. 6. Signals which are time serially obtained are processed by a digital processor 300 which receives the signals from AID converter 101. The digital processor 300 comprises an SN computer 301, a comparator 303, a delay device B 302, and a threshold-A storage device 304. Digital filtering processing is time serially performed in the SN computer 301. The SN computer 301 performs the above-described basic processing, and removes signals other than a foreign-matter signal.

Figure 8:
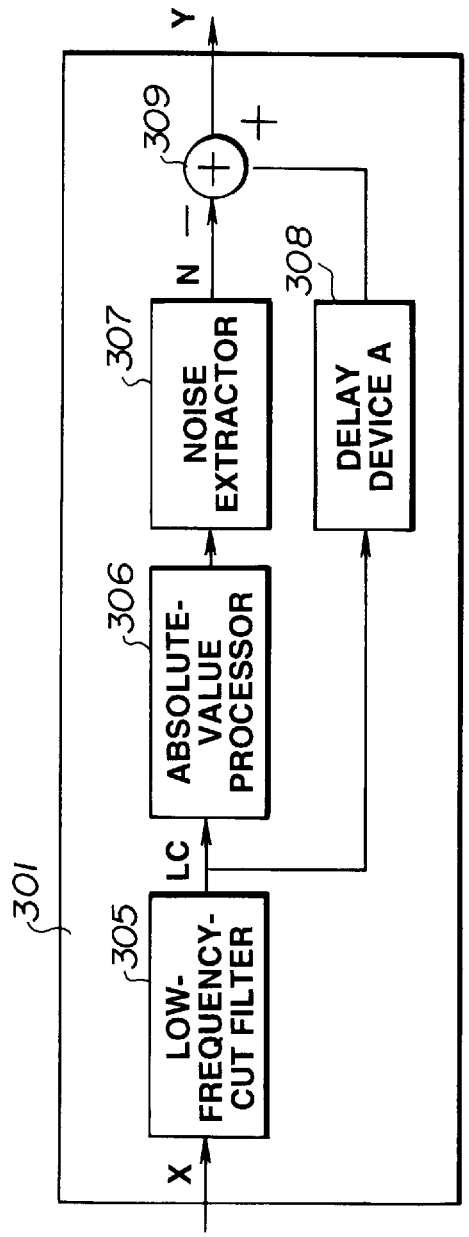
FIG. 8 is a schematic block diagram illustrating the detailed configuration of a signal processing system of the fourth embodiment.

The internal configuration of the SN computer 301 will now be described in detail with reference to FIG. 8. Timeserial signals X(t) obtained as digital information by the AID converter 101 are time serially processed according to the above-described expression (12) by a low-frequency-cut filter 305, which comprises an FIR (finite-duration impulseresponse) filter or the like.

The outputs LC(t) of the low-frequency-cut filter are output as the absolute values |LC(t)|from an absolute-value processor 306. The absolute values|LC(t)|become time-serial input signals for a noise extractor 307, which extracts noise components N(t). The absolute-value processor 306 and the noise extractor 307 perform processing according to the above-described expression (13).

In order to perform processing according to the above-described expression (14), The value of LC(t)–N(t) is calculated. At that time, the value LC(t) obtained at the same time as the value N(t) is used. When performing subtraction, since the signal is delayed by a few stages of noise extraction filters, the phase of N(t) does not coincide with the phase of LC(t). Hence, the phase of the output of LC(t) is adjusted using a delay device A 308. The subtraction is performed by an adder 309. From among the inputs to the adder 309, the sign of the output of the noise extractor 307 is inverted. Although inversion of the sign of the output of the noise extractor is easily performed by making all filter coefficients of the noise extractor 307 minus, a sign inverter may be used, or a subtracter may be used instead of the adder 309. processing when Y(t)<0 shown in the abovedescribed expression (15) is performed by the comparator 303.

Filter coefficients and the numbers of filters of the low-frequency-cut filter 305 and the noise extractor 307, and the number of elements of the delay device A 308 are preset by the controller 100.

Next, a description will be provided of the role of the comparator 303. The above-described processing (Y(t)=LC(t)–N(t)) is effective for detection of a foreign particle providing very weak scattered light. However, this processing is not always necessary when the size of a particle is large, for example, equal to or greater than 0.6μm. In some cases, linearity in detection may not be maintained. Accordingly, when a value obtained by performing A/D conversion of a signal from the detector 9 is greater than a preset voltage value, the output value after A/D conversion is used without modification. For example, if an output voltage of the A/D converter 101 obtained from light reflected from a foreign particle having a size of 0.6μm is 0.5 V, the output X(t) after A/D conversion is used. The comparator 303 performs switching between Y(t) and X(t). That is, the comparator 303 compares the threshold A stored in the threshold-A storage device 304 with the output X(t) after A/D conversion. When the threshold A is smaller than the output X(t) after A/D conversion, the result Y(t) of the SN computer 301 is selected. When the threshold A is greater than the value X(t), the output X(t) after A/D conversion is selected.

When performing comparison, the result Y(t) of processing of the output X(t) after A/D conversion by the SN computer 301 produces a delay corresponding to a few stages. Hence, the delay is adjusted by a delay device B 302. The border line for selecting X(t) or Y(t) can be arbitrary set by the threshold A. As for the processing when Y(t)<0, 0 is output when the output of the comparator 303 is negative.

In the present embodiment, various filter coefficients can be considered. For the purpose of removing signals other than a foreign-matter signal, there is no limitation in filter coefficients and the value of the threshold A stored in the threshold-A storage device 304. It is, of course, possible to select only the results of filtering processing, or to select only values after A/D conversion by setting an appropriate threshold.

Fifth Embodiment

Next, a description will be provided of a fifth embodiment of the present invention. First, problems to be solved in the fifth embodiment will be described.

Figure 11:
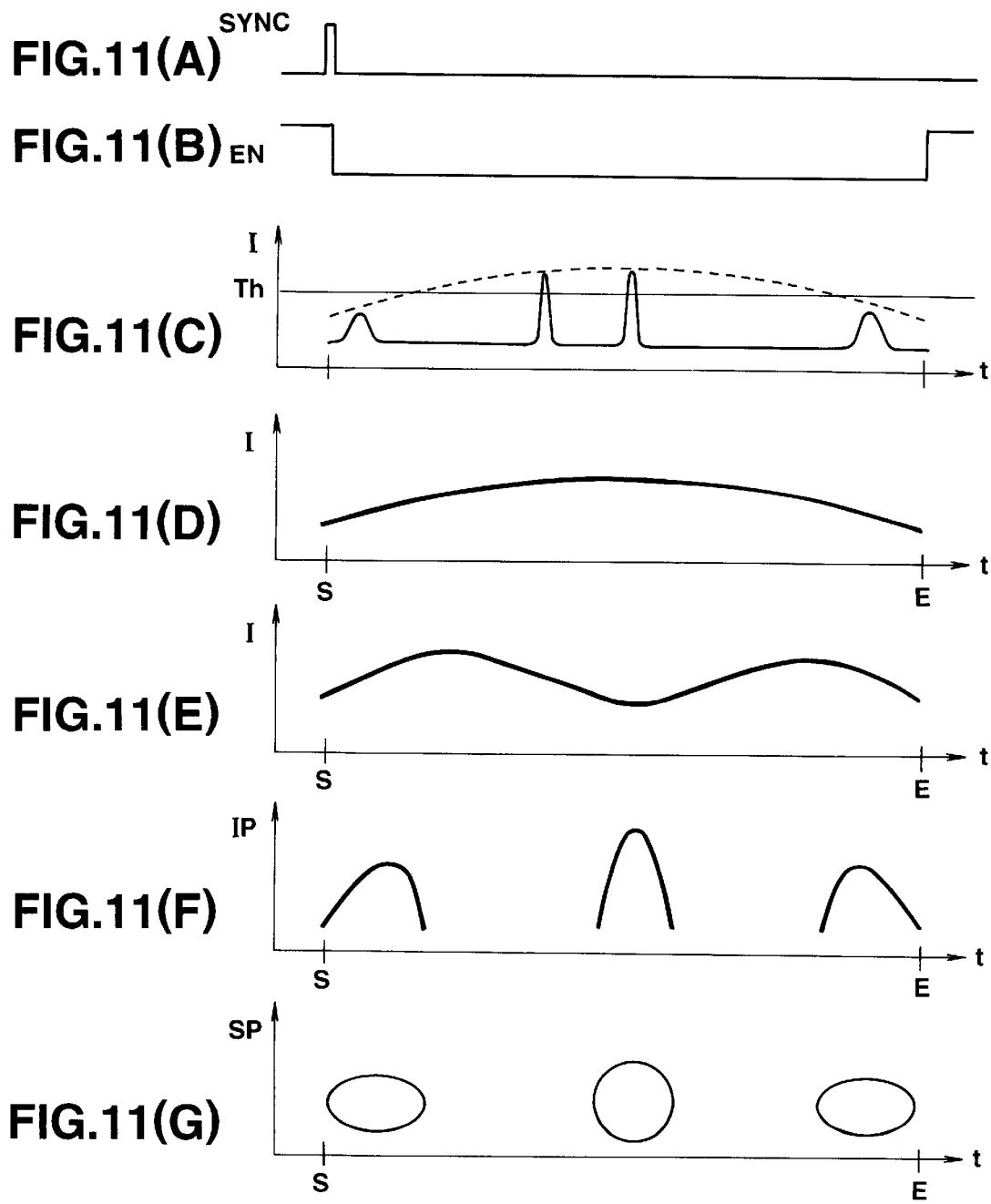
FIGS. 11(a) through 11(g) are graphs illustrating problems to be solved in the fifth embodiment.

When performing inspection by scanning a surface to be inspected by a laser beam, as shown in FIGS. 11(d) and 11(e), even if foreign matter having the same particle size is scanned, a difference is produced between the levels of signals obtained by photoelectric conversion depending on the scanning positions of the laser beam. In FIGS. 11(d) and 11(e), the abscissa represents the scanning position (time t), and the ordinate represents the signal level (I) after photoelectric conversion. In addition, S represents the beginning of scanning and F represents the end of scanning. The reasons for the difference are as follows. That is, even if a subtrate to be inspected is scanned by a laser beam having a constant intensity, as shown in FIG. 11(f), the intensity distribution (Ip) of the illuminating spot of the laser beam changes depending on the scanning position, or, as shown in FIG. 11(g), the illuminating region (Sp) of the illuminating spot of the laser beam changes depending on the scanning position. When the intensity of the laser beam changes as shown in FIG. 11(f) or 11(g), signal levels as shown in FIG. 11(d) are obtained. This is due to aberrations in the scanning optical system, defocusing and the like. Signal levels as shown in FIG. 11(e) are also possible depending on characteristics of the optical system. When performing discrimination of foreign matter with a constant threshold, even if foreign particles having the same particle size are present on the substrate to be inspected, for example, in the case of FIG. 11(c), it is determined that no foreign matter is present in the vicinity of the circumference, thereby causing an error in detection.

In the present embodiment, in order to solve the above-described problems, the presence of foreign matter is exactly determined by arranging the apparatus such that the intensity of the signal from foreign matter is constant irrespective of the scanning position. Detailed signal processing procedures for achieving this goal will now be described. In order to emphasize a signal from foreign matter, filtering processing of passing only a signal having a Gaussian distribution is performed. Accordingly, random information, such as noise information, is removed. The filtering processing is performed as follows:

$$Y(t) = \sum_{i=-n}^{n} X(t+i)F(i). \quad (16)$$

This expression indicates the correlation between templates of 2n+1 points and signal data, where F(i) represents filter coefficients, X(t) represents signal data after A/D conversion by A/D converter 101, and Y(t) represents the result of filtering.

In order to shorten the processing time period, the interval between filter coefficients is lengthened, and the following calculation is performed:

$$Y(t) = \sum_{i=-n}^{n} X(t+i*p)F(i). \quad (17)$$

Since the interval between filter coefficients is multiplied by p, the number of filter coefficients, i.e., the filter size is reduced to 1/p compared with the case of expression (16). The filter coefficient is changed depending on the scanning position. Thus, Y(t) becomes $$Y(t) = \sum_{i=-n}^{n} X(t+i*p)Ft(i), \quad (18)$$

where Ft(i) is the filter coefficient changed depending on the scanning position. The values of n and p are also changed depending on the scanning position.

Figure 10:
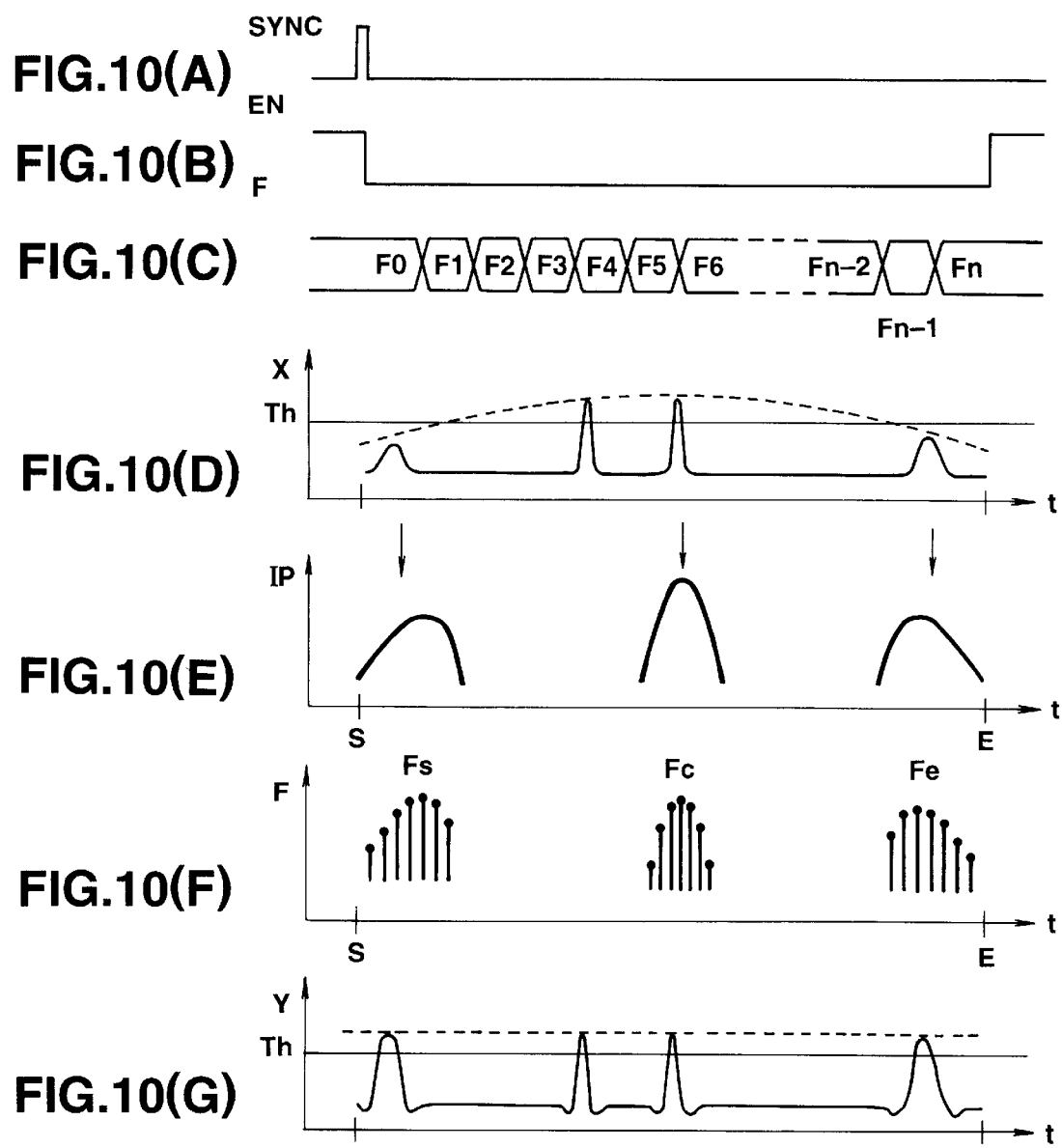
FIGS. 10(a) through 10(g) are graphs illustrating results of signal processing in the fifth embodiment.

The effects of filtering in which the filter coefficient is changed depending on the scanning position will now be described with reference to FIGS. 10(a)–10(g). When foreign particles having the same particle size are scanned by a laser beam having the intensity distribution shown in FIG. 11(f) and photoelectric conversion is performed, time serial signals X(t) as shown in FIG. 10(d) are obtained. Foreign matter cannot be detected in the vicinity of scanning ends if a constant threshold (Th) is set for such signals.

FIG. 11(e) illustrates enlarged shapes of foreignmatter signals at the start point, the middle point and the end point of scanning. Each of the shapes ressembles the intensity distribution of the laser beam because of the above-described reason.

Accordingly, filter coefficients having the characteristics shown in FIG. 10(f) are adopted.

In the vicinity of the start position of scanning, Fs(−9)=−4, Fs(−6)=−2, Fs(−3)=1, Fs(0) =3, Fs(3)=2, Fs(6)=1, and Fs(0)=−1.

In the vicinity of the middle point of scanning, Fc(−6)=−1.5, Fc(−4)=−1, Fc(−2)=1, Fc(0)=3, Fc(2)=1, Fc(4)=−1, and Fc(6)=−1.5.

In the vicinity of the end point of scanning, Fe(−9)=−1, Fe(−6)=1, Fe(−3)=2, Fe(0)=3, Fe(3) =1, Fe(6)=−2, and Fe(9)=−4.

These filter coefficients have the following characteristics.

First, utilizing the chracteristics that the signal intensity distribution is Gaussian and noise is random, filter coefficients to emphasize only a signal from foreign matter and to remove noise are provided.

Second, in the vicinity of the ends of scanning, since the signal intensity distribution is broad, the range of filtering is also broad. On the other hand, in the vicinity of the center of scanning, since the signal intensity distribution is sharp, the range of filtering is also sharp.

Third, in the vicinity of the ends of scanning, since the signal distribution is unsymmetrical, the filter characteristics are also unsymmetrical. On the other hand, in the vicinity of the center of scanning, since the signal intensity distribution is symmetrical, the filter characteristics are also symmetrical. The filter characteristics are arranged such that the signal levels at the ends of scanning are relatively increased with respect to the signal levels at the center of scanning.

FIG. 10(g) illustrates a result of processing when filter setting corresponding to the signal shown in FIG. 10(d) is performed. The same signal level is obtained at the ends of scanning and the center of scanning, and signal levels at the ends of scanning are increased to such a level that no problem arises (i.e., foreign matter is detected) even if foreign matter is discriminated with a constant threshold. The difference between the widths of signals causes no problem in the discrimination of foreign matter.

Figure 9:
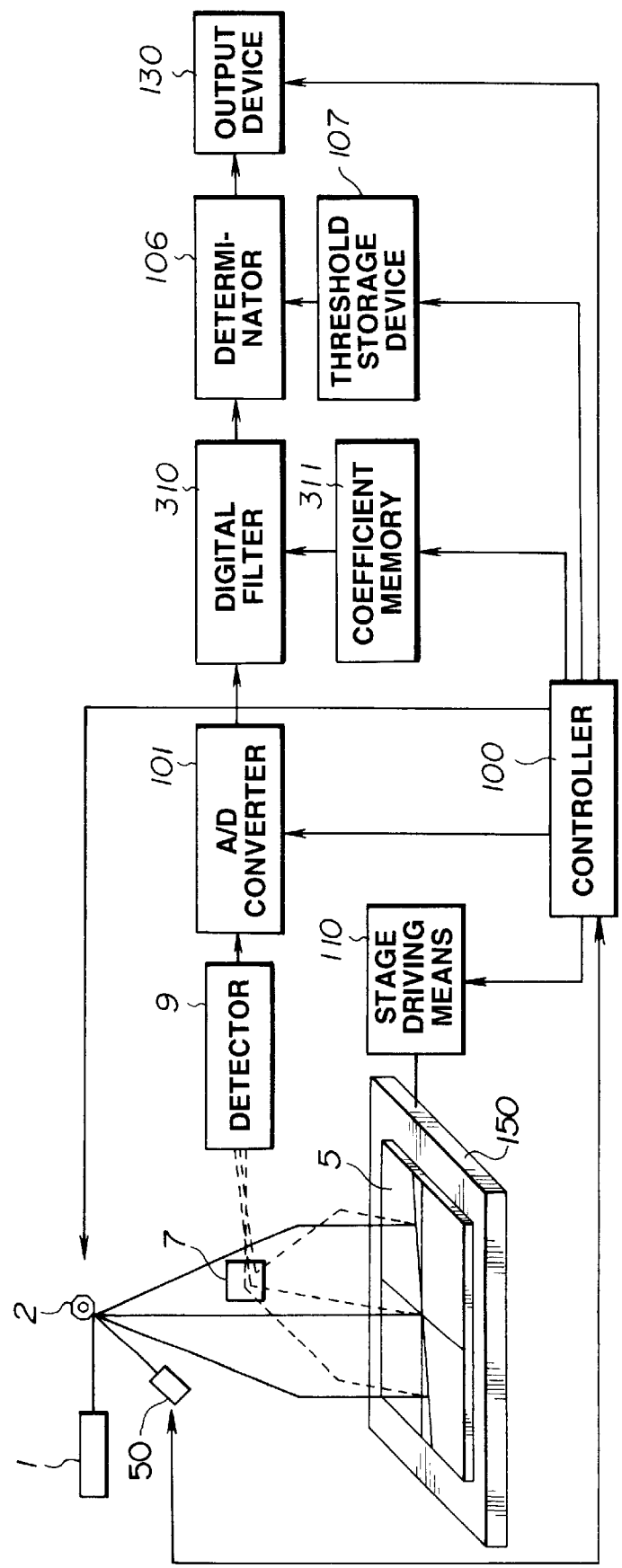
FIG. 9 is a schematic block diagram illustrating the configuration of an apparatus for inspecting foreign matter on a reticle according to a fifth embodiment of the present invention.

Next, the configuration of the signal processing unit of the present embodiment will be described in detail. In FIG. 9, a laser beam deflected by a polygonal mirror 2 generates a synchronizing signal SYNC (see FIG. 10(a)) when it is incident upon a photosensor 50, and a signal-processing start signal EN is formed (see FIG. 10(b)). The period of the EN signal has a known value predetermined by the number of revolutions of a motor for rotating the polygonal mirror 2 and the number of faces of the polygonal mirror 2. Upon generation of the EN signal, a controller 100 generates a timing signal to start A/D conversion. At the same time, a bank is set in a coefficient memory 311 for storing coefficients of a digital filter 310 in response to an instruction from controller 100. Information stored in the coefficient memory 311 is transferred to a memory of the digital filter 310, where filter coefficients are set. The initial bank of the coefficient memory 311 is $F_o$. As shown in FIG. 10(c), in synchronization with the rotation of the polygonal mirror 2, the bank in the coefficient memory 311 is changed to $F_o$, $F_1$, $F_2$, . . . in accordance with scanning positions at a constant time interval. In accordance with changes in the bank in the coefficient memory 311, coefficients of the digital filter 310 are changed. By thus changing filter coefficients of the digital filter 311, changes in the signal level depending on scanning positions are prevented. The above-described filter coefficients $F_s$, $F_c$ and $F_e$ correspond to banks on the time base in FIGS. 10(a)–10(g) as $F_o = F_s$, $F_6 = F_c$, and $F_n = F_e$.

Sixth Embodiment

Figure 12:
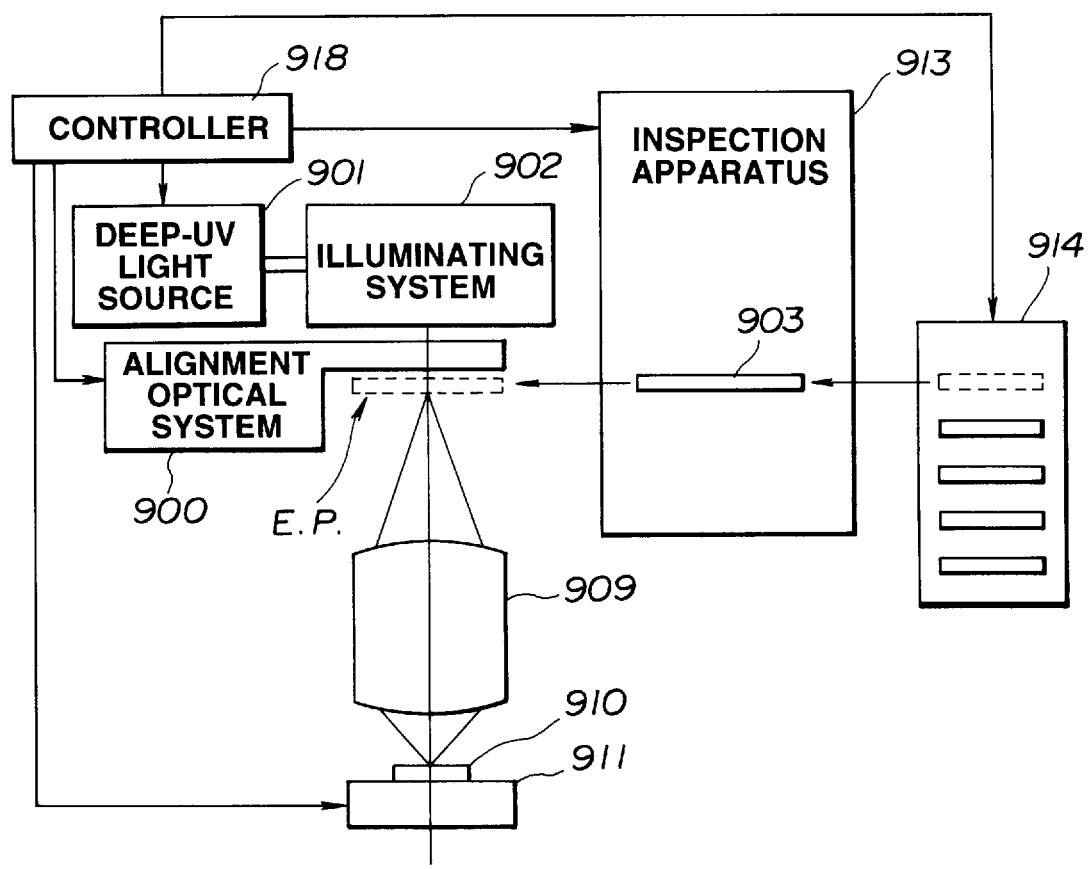
FIG. 12 is a schematic block diagram illustrating the configuration of an exposure apparatus including an inspection apparatus according to a sixth embodiment of the present invention.

FIG. 12 is a diagram illustrating a system for manufacturing semiconductor devices by printing a circuit pattern on an original, such as a reticle, a photomask or the like, onto a silicon wafer according to a sixth embodiment of the present invention. The system grossly comprises an exposure apparatus, an original accommodating apparatus, an original inspection apparatus, and a controller. These apparatuses are disposed in a clean room.

A deep-UV light source 901 comprises for example, an examiner laser. An illuminating system 902 simultaneously (at the same time) illuminates an original set at an exposure position E.p. from above with a predetermined NA (numerical aperture). Reference numeral 909 represents an ultra-highresolution lens system (or mirror system) for transferring a circuit pattern formed on the original onto a silicon wafer 910. During a printing operation, exposure is repeated while shifting the wafer 910 in units of a shot according to a stepped movement of a moving stage 911. Reference numeral 900 represents an alignment optical system for aligning the original with the wafer 910 before starting an exposure operation, and includes at least one microscope system for observing the original. These components constitute an exposure apparatus.

Reference numeral 914 represents an original accommodating apparatus, which accommodates a plurality of originals. Reference numeral 913 represents an original inspection apparatus, which has the configuration of one of the above-described embodiments. The original inspection apparatus 913 inspects foreign matter on a selected original before the original is taken out from the original accommodating apparatus 914 and is set at the exposure position E.p. The principle and the operation of inspection of foreign matter are the same as in one of the above-described embodiments. A controller 918 controls sequences of the entire system, such as operation instructions for the original accommodating apparatus 914 and the original inspection apparatus 913, and alignment, exposure, stepped feeding of the wafer, and the like which are the basic operations of the exposure apparatus.

A description will now be provided of production processes of semiconductor devices using the system of the present embodiment. First, an original to be used is taken out from the original accommodating apparatus 914, and is set in the original inspection apparatus 91w. Then, the original inspection apparatus 913 inspects foreign matter on the original. When it has been confirmed that no foreign matter is present on the original, the original is set at the exposure position E.p. in the exposure apparatus. Then, the silicon wafer 910, serving as an object to be exposed, is set on the moving stage 911. Exposure is repeated by performing reduction projection of the pattern on the original onto each region of the silicon wafer 910 while shifting the wafer 910 in units of a shot in accordance with a stepped feeding of the moving stage 911, according to a step-andrepeat method. When exposure on one silicon wafer has been completed, the wafer is accommodated, a new silicon wafer is supplied, and exposure of the pattern on the original is repeated by the step-and-repeat method in the same manner.

The silicon wafer after exposure is subjected to processing, such as development, packaging and the like, using apparatuses provided separated from this system. Thereafter, semiconductor devices are manufactured after passing through an assembling process, comprising dicing, wire bonding, packaging and the like. According to the present embodiment, highly integrated semiconductor devices having very fine circuit patterns which have previously been difficult to manufacture can be manufactured.

Seventh Embodiment

Figure 13:
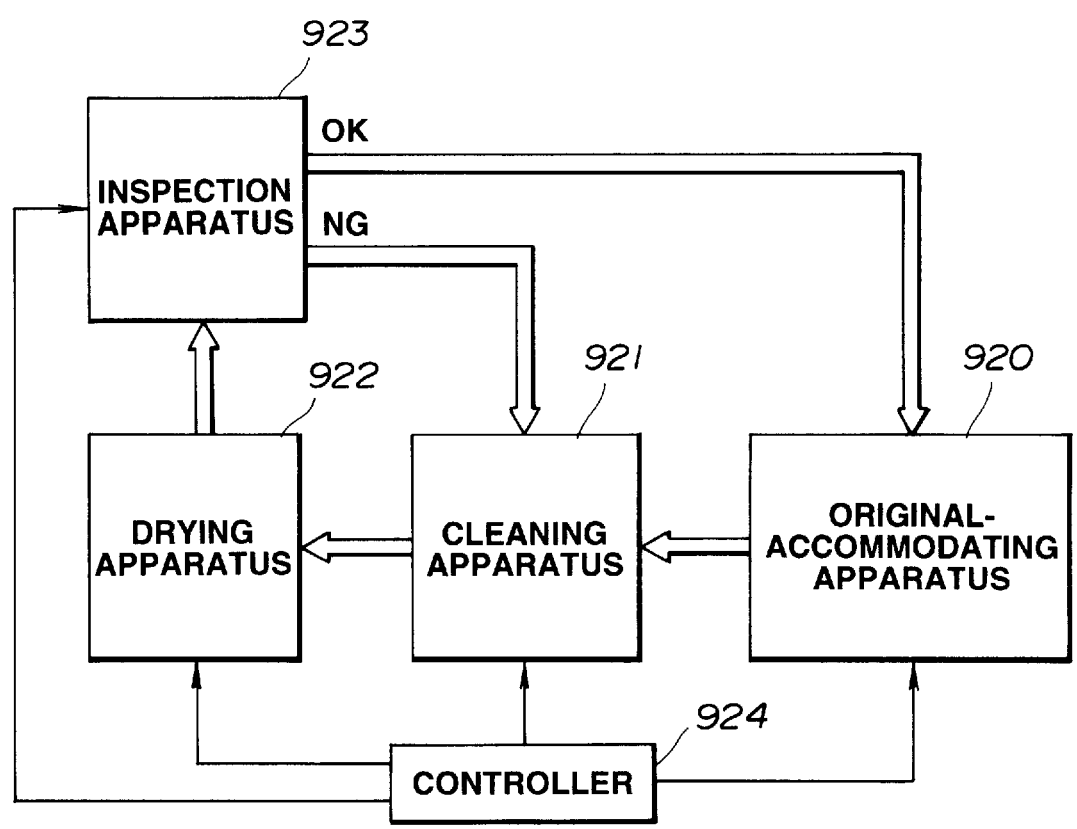
FIG. 13 is a schematic block diagram illustrating the configuration of a cleaning apparatus including an inspection apparatus according to a seventh embodiment of the present invention.
Figure 14:
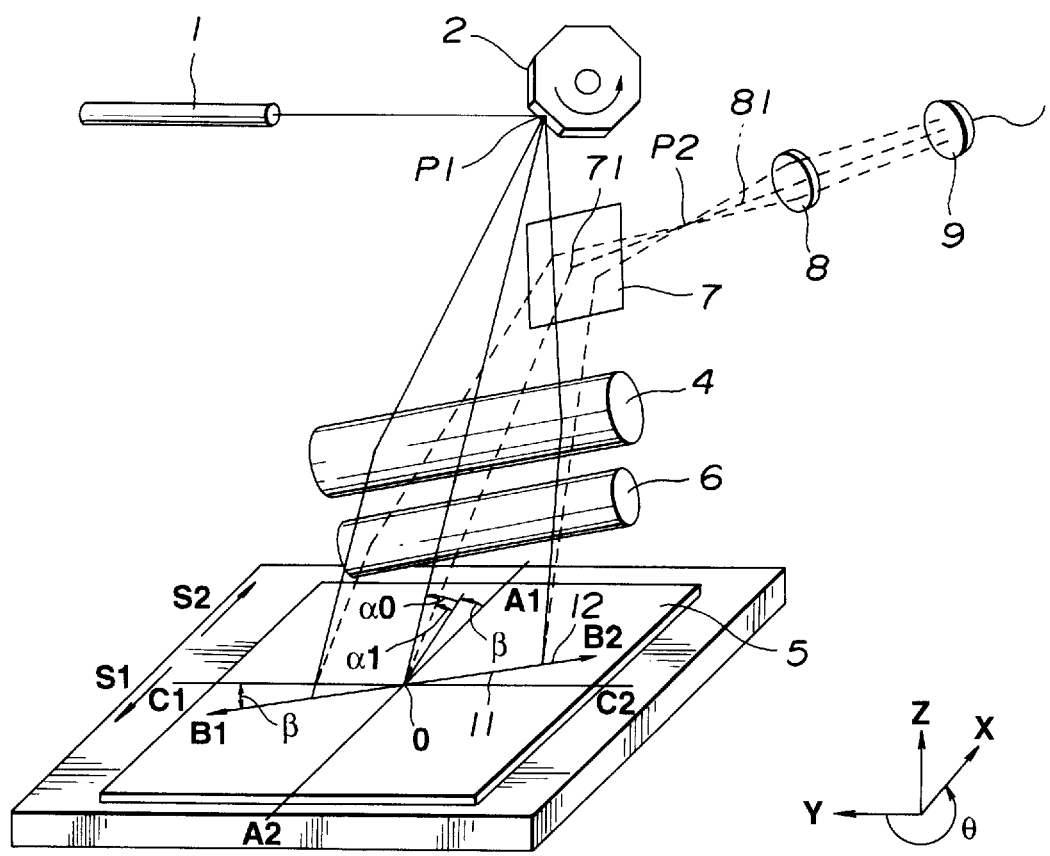
FIG. 14 is a schematic diagram illustrating an optical system of a conventional apparatus for inspecting foreign matter on a reticle.
Figure 15A:
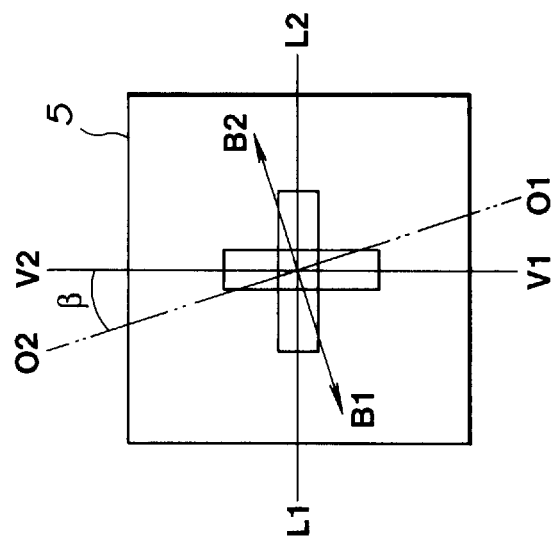
FIGS. 15(A) and 15(B) are schematic diagrams illustrating the detail of a portion of the apparatus shown in FIG. 14.
Figure 15B:
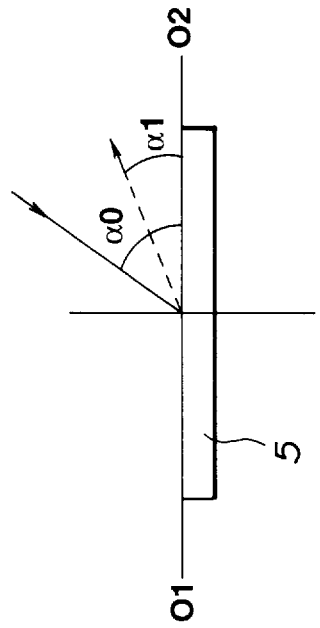

FIG. 13 is a diagram illustrating a cleaning/inspection system for manufacturing semiconductor devices according to a seventh embodiment of the present invention. The system grossly comprises an original accommodating apparatus, a cleaing apparatus, a drying apparatus, an inspection apparatus and a controller, which are disposed within a clean chamber.

An original accommodating apparatus 920 accommodates a plurality of originals, and supplies an original to be cleaned. A cleaning apparatus 921 cleans the original using pure water. A drying apparatus 922 dries the cleaned original. An original inspection apparatus 923 includes the configuration of one of the above-described embodiments, and inspects foreign matter on the cleaned original according to the method of one of the above-described embodiments. A controller 924 performs sequence control of the entire system.

A description will now be provided of operations of the system. First, an original to be cleaned is taken out from the original accommodating apparatus 920, and supplies the cleaning apparatus 921 with the original. The original cleaned by the cleaning apparatus 921 is sent to the drying apparatus 922 and is dried. After drying the original, the original is sent to the inspection apparatus 923, which inspects foreign matter on the original according to the method of one of the above-described embodiments. When no foreign matter has been confirmed as a result of inspection, the original is returned to the original accommodating apparatus 920. When foreign matter has been confirmed as a result of inspection, the original is returned to the cleaning apparatus 921. After cleaning and drying operations, the original is inspected again. This processing is repeated until foreign matter is completely removed. The original which has been completely cleaned is returned to the original accommodating apparatus 920.

Thereafter, the cleaned original is set in an exposure apparatus, and semiconductor devices are manufactured by printing a circuit pattern formed on the original onto a silicon wafer. It is thereby possible to manufacture highly integrated semiconductor devices having a very fine circuit pattern which have previously been difficult to manufacture.

The individual components shown in outline or designated by blocks in the drawings are all well known in the inspection apparatus, exposure apparatus and device manufacturing method arts and their specific construction andd operation are not critical to the operation or the best mode for carrying out the invention.

While the present invention has been described with respect to what is presently considered to be the preferred embodiments, it is to be understood that invention is not limited to the disclosed embodiments. To the contrary, the present invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An inspection apparatus for inspecting foreign matter on the substrate, said apparatus comprising:

illuminating means for projecting a light beam having a predetermined distribution intensity onto the substrate having a predetermined pattern formed thereon and foreign matter thereon;

light sensing means for sensing light from the substrate and photoelectrically converting the light to an electrical signal, the electrical signal having a pattern signal component representing light from the predetermined pattern and a foreign matter signal component, representing light from foreign matter on the substrate;

converting means for converting the electrical signal output by said light sensing means into a digital signal having a pattern signal component and a foreign matter signal component; and processing means for emphasizing the digital foreign matter signal component as compared to the digital pattern signal component by performing calculation processing on the digital signal based on treating the foreign matter signal component as a specific distribution determined by the predetermined distribution and treating the pattern signal component as a random noise signal.

2. An apparatus according to claim 1, wherein said processing means performs at least one of template matching processing, signal extraction processing, and noise extraction processing on the digital signal.

3. An apparatus according to claim 2, wherein said processing means performs template matching processing using templates having the shape of substantially a Gaussian distribution.

4. An apparatus according to claim 2, wherein said processing means calculates the difference between the top and the bottom levels of the digital signal.

5. An apparatus according to claim 2, wherein said processing means detects the pattern signal component using the difference between signal levels of the digital signal at positions symmetrical with respect to the center of the digital signal, performs template matching processing for the digital signal, and performs an operation on the detected pattern signal component and the result of the template matching processing.

6. An apparatus according to claim 2, wherein said processing means detects the pattern signal component using the difference between signal levels of the digital signal at positions symmetrical with respect to the center thereof, detects the foreign matter signal component using the difference between the top and the bottom levels of the digital signal, and performs an operation on the detected pattern signal component and the detected foreign matter signal component.

7. An apparatus according to claim 2, wherein said processing means detects the pattern signal component using the difference between signal levels of the digital signal at positions symmetrical with respect to the center thereof, detects the foreign matter signal component using the difference between the top and the bottom levels of the digital signal, performs template matching processing for the digital signal, and performs an operation on the foreign matter signal component, the pattern signal component, and the result of the template matching processing.

8. An apparatus according to claim 1, wherein said processing means removes a low-frequency component of the digital signal by digital filtering processing, removes noise from the digital signal, after the low-frequency component is removed therefrom, by digital filtering processing, and calculates the difference between the results of low-frequency component removal processing and noise removal processing.

9. An apparatus according to claim 8, wherein said processing means performs its processing when the digital signal is smaller than a predetermined value.

10. An apparatus according to claim 1, wherein said processing means peforms digital filtering processing using variable filter coefficients.

11. An apparatus according to claim 10, wherein said processing means changes the coefficients and the calculation method depending on a scanning position of an element scanning the substrate with the light beam.

12. An apparatus according to any one of claims 1 through 11, wherein said processing means comprises a central processing unit or a digital signal processor.

13. An exposure apparatus comprising:

an inspection apparatus for inspecting foreign matter on a substrate, said apparatus comprising:

illuminating means for projecting a light beam having a predetermined distribution intensitv onto the substrate having a predetermined pattern formed thereon and foreign matter thereon;

light sensing means for sensing light from the substrate and photoelectrically converting the light to an electrical signal, the electrical signal having a pattern signal component representing light from the predetermined pattern, and a foreign matter signal component, representing light from foreign matter on the substrate;

converting means for converting the electrical signal output by said light sensing means into a digital signal having a pattern signal component and a foreign matter signal component; and processing means for emphasizing the digital foreign matter signal component as compared to the digital pattern signal component by performing calculation processing on the digital signal based on treating the foreign matter signal component as a specific distribution determined by the predetermined distribution and treating the pattern signal component as a random noise signal for discriminating the digital foreign matter signal component from the digital pattern signal component; and means for performing exposure and transfer processing using the inspected substrate inspected by said inspection apparatus.

14. The exposure apparatus according to claim 13, wherein said processing means performs at least one of template matching processing, signal extraction processing, and noise extraction processing on the digital signal.

15. The exposure apparatus according to claim 14, wherein said processing means performs template matching processing using templates having the shape of substantially a Gaussian distribution.

16. The exposure apparatus according to claim 14, wherein said processing means calculates the difference between the top and the bottom levels of the digital signal.

17. The exposure apparatus according to claim 14, wherein said processing means detects the pattern signal component using the difference between signal levels of the digital signal at positions symmetrical with respect to the center of the digital signal, performs template matching processing for the digital signal, and performs an operation on the detected pattern signal component and the result of the template matching processing.

18. The exposure apparatus according to claim 14, wherein said processing means detects the pattern signal component using the difference between signal levels of the digital signal at positions symmetrical with respect to the center thereof, detects the foreign matter signal component using the difference between the top and the bottom levels of the digital signal, and performs an operation on the detected pattern signal component and the detected foreign matter signal component.

19. The exposure apparatus according to claim 14, wherein said processing means detects the pattern signal component using the difference between signal levels of the digital signal at positions symmetrical with respect to the center thereof, detects the foreign matter signal component using the difference between the top and the bottom levels of the digital signal, performs template matching processing for the digital signal, and performs an operation on the foreign matter signal component, the pattern signal component, and the result of the template matching processing.

20. The exposure apparatus according to claim 13, wherein said processing means removes a low-frequency component of the digital signal by digital filtering processing, removes noise from the digital signal, after the low-frequency component is removed therefrom, by digital filtering processing, and calculates the difference between the results of low-frequency component removal processing and noise removal processing.

21. The exposure apparatus according to claim 20, wherein said processing means performs its processing when the digital signal is smaller than a predetermined value.

22. The exposure apparatus according to claim 13, wherein said processing means peforms digital filtering processing using variable filter coefficients.

23. The exposure apparatus according to claim 22, wherein said processing means changes the coefficients and the calculation method depending on a scanning position of an element scanning the substrate with the light beam.

24. The exposure apparatus according to any one of claims 13–23, wherein said processing means comprises a central processing unit or a digital signal processor.

25. A method for inspecting foreign matter on a substrate, said method comprising the steps of:
projecting a light beam having a predetermined distribution intensity onto the substrate having a predetermined pattern formed thereon and foreign matter thereon;
sensing light from the substrate and photoelectrically converting the light to an electrical signal having a pattern signal component representing light from the predetermined pattern and a foreign matter signal component representing light from foreign matter on the substrate;
converting the electrical signal produced in said sensing step into a digital signal having a pattern signal component and a foreign matter signal component; and
emphasizing the digital foreign matter signal component as compared to the digital pattern signal component by performing calculation processing on the digital signal based on treating the foreign matter signal component as a specific distribution determined by the predetermined distribution and treating the pattern signal component as a random noise signal.

26. The method recited by claim 25, wherein said performing step performs one of template matching processing, signal extraction processing, and noise extraction processing on the digital signal.

27. The method recited by claim 26, wherein said processing step performs template matching processing using templates having the shape of substantially a Gaussian distribution.

28. The method recited by claim 26, wherein said processing step calculates the difference between the top and the bottom levels of the digital signal.

29. The method recited by claim 26, wherein said processing step comprises the steps of:
detecting the pattern signal component using the difference between signal levels of the digital signal at positions symmetrical with respect to the center thereof;
performing template matching processing for the digital signal; and
performing an operation on the detected pattern signal component and the result of the template matching processing.

30. The method recited by claim 26, wherein said processing step comprises the steps of:
detecting the pattern signal component using the difference between signal levels of the digital signal at positions symmetrical with respect to the center thereof;
detecting the foreign matter signal component using the difference between the top and the bottom levels of the digital signal; and
performing an operation on the detected pattern signal component and the detected foreign matter signal component.

31. The method recited by claim 26, wherein said processing step comprises the steps of:
detecting the pattern signal component using the difference between signal levels of the digital signal at positions symmetrical with respect to the center thereof;
detecting the foreign matter signal component using the difference between the top and the bottom levels of the digital signal;
performing template matching processing for the digital signal; and
performing an operation on the foreign matter signal component, the pattern signal component, and the result of the template matching processing.

32. The method recited by claim 25, wherein said processing step comprises the steps of:
removing a low-frequency component of the digital signal by digital filtering processing;
removing noise from the digital signal, after the lowfrequency component is removed therefrom, by digital filtering processing; and
calculating the difference between the results of lowfrequency component removal processing and noise removal processing.

33. The method recited by claim 32, wherein said processing step performs its processing when the digital signal is smaller than a predetermined value.

34. The method recited by claim 25, wherein said processing step peforms digital filtering processing using variable filter coefficients.

35. The method recited by claim 34, wherein said processing step changes the coefficients and the calculation method depending on a scanning position of an element scanning the substrate with the light beam.

36. The method recited by any one of claims 25 through 34, further comprising the step of performing said processing step with a central processing unit or a digital signal processor.

37. The method recited by claim 25, further comprising the steps of:

inspecting the substrate using said projecting, sensing, converting, and performing steps; and performing exposure and transfer processing using the substrate inspected in said inspecting step.

38. The method recited by claim 37, further comprising the steps of:

manufacturing devices using the substrate subjected to said inspecting, and exposure and transfer processing steps.

* * * * *

UNITED STATES PATENT AND TRADEMARK OFFICE
CERTIFICATE OF CORRECTION

PATENT NO.   : 5,774,575
DATED        : June 30, 1998
INVENTOR(S)  : HIROSHI TANAKA, ET AL.

It is certified that error appears in the above-identified patent and that said Letters Patent is hereby corrected as shown below:

COLUMN 2:

Line 49, "Examiner" should read --excimer--.

COLUMN 6:

Line 20, "pS" should read --PS--;
   Line 29, "processing" (first occurrence) should read --Processing--; and
   Line 58, "processing" (first occurrence) should read --Processing--.

COLUMN 7:

Line 17, "processing" (first occurrence) should read --Processing--.

COLUMN 9:

Line 27, "CpU" should read --CPU--; and
   Line 58, "FIG. 5" should begin a new paragraph.

COLUMN 10:

Line 35, "FIG. 6" should begin a new paragraph.

UNITED STATES PATENT AND TRADEMARK OFFICE
CERTIFICATE OF CORRECTION

PATENT NO.   : 5,774,575
DATED        : June 30, 1998
INVENTOR(S)  : HIROSHI TANAKA, ET AL.

It is certified that error appears in the above-identified patent and that said Letters Patent is hereby corrected as shown below:

COLUMN 11:

Line 12, "Within" should begin a new paragraph;
   Line 35, "abovedescribed" should read --above-described--;
   Line 53, "pS" should read --PS--;
   Line 58, "pS" should read --PS-- and "pS." should read --PS.--; and
   Line 66, "AID" should read --A/D--.

COLUMN 12:

Line 9, "AID" should read --A/D--;
   Line 12, "impulseresponse)" should read --impulse-response)--; and
   Line 33, "abovedescribed" should read --above-described--.

COLUMN 13:

Line 30, "(Sp)" should read --(SP)--.

COLUMN 14:

Line 24, "foreignmatter" should read --foreign-matter--.

UNITED STATES PATENT AND TRADEMARK OFFICE
CERTIFICATE OF CORRECTION

PATENT NO.  : 5,774,575

DATED       : June 30, 1998

INVENTOR(S) : HIROSHI TANAKA, ET AL.

It is certified that error appears in the above-identified patent and that said Letters Patent is hereby corrected as shown below:

COLUMN 15:

Line 24, "$F_s$, $F_c$, and $F_e$" should read --Fs, Fc and Fe--;

Line 25, "$F_o=F_s, F_6=F_e,$ and $F_n=F_e$" should read --$F_0$ = Fs, $F_6$ = Fc, and $F_n$ = Fe.--;

Line 40, "ultra-highresolution" should read --ultra-high-resolution--; and

Line 57, "E.p." should read --E.P.--.

COLUMN 16:

Line 3, "91w." should read --913.--;

Line 7, "E.p." should read --E.P.--;

Line 13, "step-andrepeat" should read --step-and-repeat--;

Line 16, close up right margin; and

Line 17, close up left margin.

COLUMN 18:

Line 35, "intensitv" should read --intensity--.

UNITED STATES PATENT AND TRADEMARK OFFICE
CERTIFICATE OF CORRECTION

PATENT NO.   :  5,774,575

DATED        :  June 30, 1998

INVENTOR(S)  :  HIROSHI TANAKA, ET AL.

It is certified that error appears in the above-identified patent and that said Letters Patent is hereby corrected as shown below:

COLUMN 20:

```
Line 62, "lowfre-" should read --low-fre---; and
Line 65, "lowfre-" should read --low-fre---.
```

Signed and Sealed this

Eighteenth Day of May, 1999

Attest:

Q. TODD DICKINSON

*Attesting Officer*   *Acting Commissioner of Patents and Trademarks*